United States Patent [19]

Spedding et al.

[11] Patent Number: 5,633,218
[45] Date of Patent: May 27, 1997

[54] HERBICIDAL BENZODIOXOLES AND BENZODIOXANES

[75] Inventors: Donna L. Spedding, Bear; Thomas M. Stevenson, Newark, both of Del.

[73] Assignee: E. I. Du Pont de Nemours and Company, Wilmington, Del.

[21] Appl. No.: 450,768

[22] Filed: May 24, 1995

[51] Int. Cl.⁶ .......................... A01N 43/54; A01N 43/30; C07D 239/70; C07D 239/94
[52] U.S. Cl. .......................... 504/228; 504/235; 504/240; 504/241; 549/362; 549/441; 544/183; 544/184; 544/279; 544/283; 544/286; 544/350; 544/353
[58] Field of Search ..................... 544/183, 184, 544/279, 283, 286, 350, 353; 549/362, 441; 504/228, 240, 241, 235

[56] References Cited

U.S. PATENT DOCUMENTS

| | | | |
|---|---|---|---|
| 5,145,959 | 9/1992 | Hubsch et al. | 544/279 |
| 5,344,944 | 9/1994 | Franckowiak et al. | 549/436 |
| 5,369,127 | 11/1994 | Burk et al. | 514/464 |
| 5,389,600 | 2/1995 | Selby et al. | 504/240 |
| 5,420,301 | 5/1995 | Ackermann et al. | 549/213 |
| 5,475,132 | 12/1995 | Pepin et al. | 560/59 |

FOREIGN PATENT DOCUMENTS

| | | | |
|---|---|---|---|
| WO93/11097 | 6/1993 | WIPO | C07C 233/15 |
| WO94/21640 | 9/1994 | WIPO | C07D 487/04 |

*Primary Examiner*—Matthew V. Grumbling

[57] ABSTRACT

Compounds of Formula I, and their N-oxides and agriculturally-suitable salts, are disclosed which are useful for controlling undesired vegetation

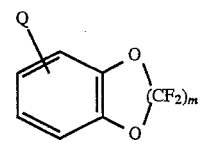

wherein:

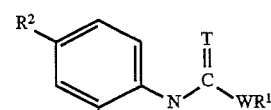

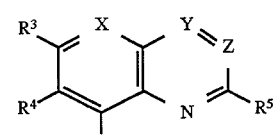

T is O or S;
W is a single bond, O, S or $NR^6$;
X is N or CH;
Y is N or CH;
Z is N or $CR^7$ provided that when Z is $CR^7$, then Y is N;
$R^6$ is H, $CH_3$ or $OCH_3$;
m is 1 or 2; and
$R^1, R^2, R^3, R^4, R^5$, and $R^7$ are as defined in the disclosure.

Also disclosed are compositions containing the compounds of Formula I and a method for controlling undesired vegetation which involves contacting the vegetation or its environment with an effective amount of a compound of Formula I.

7 Claims, No Drawings

HERBICIDAL BENZODIOXOLES AND BENZODIOXANES

BACKGROUND OF THE INVENTION

This invention relates to certain benzodioxoles and benzodioxanes, their N-oxides, agriculturally-suitable salts and compositions, and methods of their use for controlling undesirable vegetation.

WO 93/11097 discloses anilides of Formula i as herbicides:

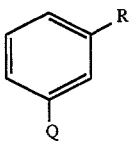

wherein

Q is, among others, Q-1

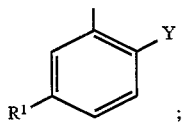

R is, among others, $C_1-C_2$ haloalkyl, $C_1-C_2$ haloalkoxy, $C_1-C_2$ haloalkylthio, halogen, cyano, or nitro;

Y is $NR^7C(O)XR^3$;

X is a single bond, O, S or $NR^4$;

$R^1$ is, among others, H, $C_1-C_3$ alkyl, $C_1-C_3$ alkoxy, $C_1-C_3$ alkylthio, $C_2-C_3$ alkoxyalkyl, $C_2-C_3$ alkylthioalkyl, halogen, $NO_2$, CN, $NHR^5$ or $NR^5R^6$; and $R^3$ is, among others, $C_1-C_5$ alkyl optionally substituted with $C_1-C_2$ alkoxy, OH, 1–3 halogens, or $C_1-C_2$ alkylthio; $CH_2(C_3-C_4$ cycloalkyl); $C_3-C_4$ cycloalkyl optionally substituted with 1–3 $CH_3$'s; $C_2-C_4$ alkenyl; or $C_2-C_4$ haloalkenyl.

U.S. Pat. No. 5,389,600 discloses heterocycles of Formula ii as herbicides:

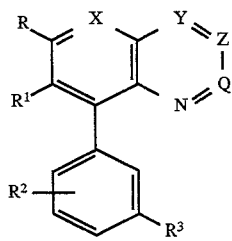

wherein

X is N or CH;

Y is N or $CR^8$;

Z is N, $CR^4$ or $CR^5$;

Q is N, $CR^4$ or $CR^5$;

R is $C_1-C_4$ alkyl, $C_2-C_4$ alkoxyalkyl, $C_2-C_4$ alkenyl, $C_2-C_4$ alkynyl, $C_1-C_4$ alkoxy, $C_1-C_4$ alkylthio, $C_1-C_3$ alkylamino or $N(C_1-C_3$ alkyl)($C_1-C_3$ alkyl);

$R^1$ is H, F, Cl or $CH_3$;

$R^2$ is H, halogen, $C_1-C_3$ alkyl, $C_1-C_3$ haloalkyl, $C_1-C_3$ alkoxy or $C_1-C_3$haloalkoxy;

$R^3$ is H, halogen, $C_1-C_4$ alkyl, $C_2-C_4$ alkenyl, $C_2-C_4$ alkynyl, $C_1-C_4$haloalkyl, $C_3-C_4$ halocycloalkyl, $C_2-C_4$ haloalkenyl, $C_2-C_4$ haloalkynyl, $OR^6$, $S(O)_nR^7$ or CN;

$R^4$ is H, CN, $C_1-C_3$ alkyl, $C_1-C_3$ alkoxy or halogen;

$R^5$ is $C_1-C_4$ haloalkyl, $C_3-C_5$ halocycloalkyl, $C_2-C_4$ haloalkenyl, $C_2-C_4$ haloalkynyl, $OR^6$, $S(O)_nR^7$ or halogen;

$R^6$ is $C_1-C_4$ alkyl, $C_3-C_4$ alkenyl, $C_3-C_4$ alkynyl, $C_1-C_4$ haloalkyl, $C_2-C_4$ haloalkenyl or $C_2-C_4$ haloalkynyl;

$R^7$ is $C_1-C_2$ alkyl or $C_1-C_2$ haloalkyl;

$R^8$ is H, CN, $C_1-C_3$ alkyl, $C_1-C_3$ alkoxy or halogen; and n is 0, 1 or 2.

WO 94/21640 discloses benzodioxoles of Formula iii as herbicides:

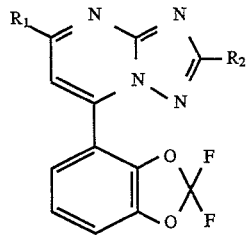

wherein $R_1$ is H, $C_1-C_4$ alkyl or $C_1-C_4$ haloalkyl; and $R_2$ is $C_1-C_4$ alkyl, $C_1-C_4$ haloalkyl, $C_1-C_4$ alkoxy, $C_{1-C4}$ haloalkoxy, $C_1-C_4$ alkylthio, $C_1-C_4$ haloalkylthio, $C_1-C_4$ alkoxy-$C_1-C_4$ alkyl, $C_1-C_4$ alkoxy-$C_1-C_4$ alkoxy, $C_1-C_4$ alkoxy-$C_1-C_4$ alkylthio, halogen, amino, $C_1-C_4$ alkylamino or $C_1-C_4$ dialkylamino.

The benzodioxoles and benzodioxanes of the present invention are not disclosed in any of these references.

SUMMARY OF THE INVENTION

This invention is directed to compounds of Formula I including all geometric and stereoisomers, N-oxides, and agriculturally suitable salts thereof, agricultural compositions containing them and their use for controlling undesirable vegetation:

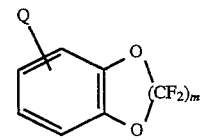

wherein

Q is

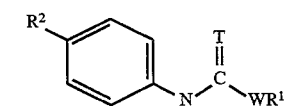

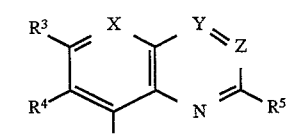

T is O or S;

W is a single bond, O, S or $NR^6$;

X is N or CH;

Y is N or CH;

Z is N or $CR^7$ provided that when Z is $CR^7$, then Y is N;

$R^1$ is $C_1-C_5$ alkyl optionally substituted with $C_1-C_2$ alkoxy, OH, 1–3 halogens, or $C_1-C_2$ alkylthio; $CH_2$ ($C_3$–$C_4$ cycloalkyl); $C_3$–$C_4$ cycloalkyl optionally substituted with 1–3 methyl groups; $C_2$–$C_4$ alkenyl; $C_2$–$C_4$ haloalkenyl; or phenyl optionally substituted with halogen, $C_1$–$C_4$ alkyl, $C_1$–$C_4$ haloalkyl, $C_1$–$C_4$ alkoxy, $C_1$–$C_4$ haloalkoxy, nitro or cyano;

$R^2$ is H, chlorine, bromine, $C_1$–$C_2$ alkyl, $C_1$–$C_2$ alkoxy, $C_1$–$C_2$ alkylthio, $C_2$–$C_3$ alkoxyalkyl, $C_2$–$C_3$ alkylthioalkyl, cyano, nitro, NH($C_1$–$C_2$ alkyl) or N($C_1$–$C_2$ alkyl)$_2$;

$R^3$ is $C_1$–$C_4$ alkyl, $C_2$–$C_4$ alkoxyalkyl, $C_2$–$C_4$ alkenyl, $C_2$–$C_4$ alkynyl, $C_1$–$C_4$ alkoxy, $C_1$–$C_4$ alkylthio, $C_1$–$C_3$ alkylamino or N($C_1$–$C_3$ alkyl)($C_1$–$C_3$ alkyl);

$R^4$ is H or F;

$R^5$ is H, CN, $C_1$–$C_3$ alkyl, $C_1$–$C_4$ haloalkyl, $C_3$–$C_4$ halocycloalkyl, $C_2$–$C_4$ haloalkenyl, $C_3$–$C_4$ haloalkynyl, $OR^8$, $S(O)_nR^9$ or halogen;

$R^6$ is H, $CH_3$ or $OCH_3$;

$R^7$ is H, CN, $C_1$–$C_3$ alkyl, $C_1$–$C_4$ haloalkyl, $C_3$–$C_4$ halocycloalkyl, $C_2$–$C_4$ haloalkenyl, $C_3$–$C_4$ haloalkynyl, $OR^{10}$, $S(O)_pR^{11}$ or halogen;

$R^8$ and $R^{10}$ are each independently $C_1$–$C_4$ alkyl, $C_3$–$C_4$ alkenyl, $C_3$–$C_4$ alkynyl, $C_1$–$C_4$ haloalkyl, $C_2$–$C_4$ haloalkenyl or $C_3$–$C_4$ haloalkynyl;

$R^9$ and $R^{11}$ are each independently $C_1$–$C_2$ alkyl or $C_1$–$C_2$ haloalkyl;

m is 1 or 2; and n and p are each independently 0, 1 or 2;

provided that when Z is $CR^7$, then exactly one of $R^5$ and $R^7$ is H.

In the above recitations, the term "alkyl", used either alone or in compound words such as "alkylthio" or "haloalkyl" includes straight-chain or branched alkyl, such as, methyl, ethyl, n-propyl, i-propyl, or the different butyl or pentyl isomers. "Alkenyl" includes straight-chain or branched alkenes such as vinyl, 1-propenyl, 2-propenyl, and the different butenyl isomers. "Alkenyl" also includes polyenes such as 1,3-butadienyl. "Alkynyl" includes straight-chain or branched alkynes such as ethynyl, 1-propynyl, 3-propynyl and the different butynyl isomers. "Alkynyl" can also include moieties comprised of multiple triple bonds such as 1,3-butadiynyl. "Alkoxy" includes, for example, methoxy, ethoxy, n-propyloxy, isopropyloxy and the different butoxy isomers. "Alkoxyalkyl" denotes alkoxy substitution on alkyl. Examples of "alkoxyalkyl" include $CH_3OCH_2$, $CH_3OCH_2CH_2$, $CH_3CH_2OCH_2$, $CH_3CH_2CH_2OCH_2$ and $CH_3CH_2OCH_2CH_2$. "Alkylthio" includes branched or straight-chain alkylthio moieties such as methylthio, ethylthio, and the different propylthio and butylthio isomers. "Alkylamino", and the like, are defined analogously to the above examples. "Cycloalkyl" includes, for example, cyclopropyl and cyclobutyl.

The term "halogen", either alone or in compound words such as "haloalkyl", includes fluorine, chlorine, bromine or iodine. The term "1–3 halogen" indicates that one, two or three of the available positions for that substituent may be halogen. Further, when used in compound words such as "haloalkyl", said alkyl may be partially or fully substituted with halogen atoms which may be the same or different. Examples of "haloalkyl" include $F_3C$, $ClCH_2$, $CF_3CH_2$ and $CF_3CCl_2$. The terms "haloalkenyl", "haloalkynyl" "haloalkoxy", and the like are defined analogously to the term "haloalkyl". Examples of "haloalkenyl" include $(Cl)_2C{=}CHCH_2$ and $CF_3CH{=}CHCH_2$. Examples of "haloalkynyl" include $HC{\equiv}CCHCl$, $CF_3C{\equiv}C$, $CCl_3C{\equiv}C$ and $FCH_2C{\equiv}CCH_2$. Examples of "haloalkoxy" include $CF_3O$, $CCl_3CH_2O$, $HCF_2CH_2CH_2O$ and $CF_3CH_2O$.

The total number of carbon atoms in a substituent group is indicated by the "$C_i$–$C_j$" prefix where i and j are numbers from 1 to 5. For example, $C_1$–$C_3$ alkylthio designates methylthio through propylthio; $C_2$ alkoxyalkyl designates $CH_3OCH_2$; $C_3$ alkoxyalkyl designates, for example, $CH_3CH(OCH_3)$, $CH_3OCH_2CH_2$ or $CH_3CH_2OCH_2$; and $C_4$ alkoxyalkyl designates the various isomers of an alkyl group substituted with an alkoxy group containing a total of four carbon atoms, examples including $CH_3CH_2CH_2OCH_2$, and $CH_3CH_2OCH_2CH_2$.

When a group contains a substituent which can be hydrogen, for example $R^2$ or $R^5$, then, when this substituent is taken as hydrogen, it is recognized that this is equivalent to said group being unsubstituted.

Compounds of this invention can exist as one or more stereoisomers. The various stereoisomers include enantiomers, diastereomers, atropisomers and geometric isomers. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate and/or to selectively prepare said stereoisomers. Accordingly, the present invention comprises compounds selected from Formula I, N-oxides and agriculturally suitable salts thereof. The compounds of the invention may be present as a mixture of stereoisomers, individual stereoisomers, or as an optically active form.

The salts of the compounds of the invention include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids. The salts of the compounds of the invention also include those formed with organic bases (e.g., pyridine, ammonia, or triethylamine) or inorganic bases (e.g., hydrides, hydroxides, or carbonates of sodium, potassium, lithium, calcium, magnesium or barium) when the compound contains an acidic group.

Preferred compounds for reasons of better activity and/or ease of synthesis are: agriculturally-suitable salts thereof, wherein:

$R^1$ is $C_1$–$C_4$ alkyl optionally substituted with methoxy or 1–3 halogens; $C_2$–$C_4$ alkenyl; or $C_2$–$C_4$ haloalkenyl;

$R^2$ is chlorine, bromine, $C_1$–$C_2$ alkyl, $C_1$–$C_2$ alkoxy, cyano, nitro, NH($C_1$–$C_2$ alkyl) or N($C_1$–$C_2$ alkyl)$_2$; and $R^3$ is $C_1$–$C_3$ alkyl, $C_2$–$C_3$ alkoxyalkyl, $C_2$–$C_3$ alkenyl, $C_2$–$C_3$ alkynyl, $C_1$–$C_3$ alkoxy, $C_1$–$C_2$ alkylthio, $C_1$–$C_2$ alkylamino or N($C_1$–$C_2$ alkyl)($C_1$–$C_2$ alkyl);

$R^7$ is H, $C_1$–$C_2$ haloalkyl, $OR^{10}$, or $S(O)_pR^{11}$;

$R^{10}$ is $C_1$–$C_2$ haloalkyl;

$R^{11}$ is $C_1$ haloalkyl; and p is 0.

Preferred 2. Compounds of Preferred 1 wherein:

T is O;

W is a single bond;

m is 1; and n is 0.

Preferred 3. Compounds of Preferred 2 wherein:

$R^5$ is H, $C_1$–$C_2$ haloalkyl, $OR^8$, or $SR^9$;

$R^7$ is H, $CF_3$, or $OR^{10}$;

$R^8$ is $C_1$–$C_2$ haloalkyl;

$R^9$ is $C_1$ haloalkyl; and $R^{10}$ is $CF_2H$.

Most preferred are compounds of Preferred 3 selected from the group:

N-[2-(2,2-difluoro-1,3-benzodioxol-4-yl)-4-methylphenyl]-2-methylpropanamide; and 8-(2,2-difluoro-1,3-benzodioxol-4-yl)-2-(difluoromethoxy)-6-methylquinoxaline.

This invention also relates to herbicidal compositions comprising herbicidally effective amounts of the compounds of Formula I and at least one of a surfactant, a solid diluent or a liquid diluent. The preferred compositions of the present invention are those which comprise the above preferred compounds.

This invention also relates to a method for controlling undesired vegetation comprising applying to the locus of the vegetation herbicidally effective amounts of the compounds of Formula I and the compositions described herein. The preferred methods of use are those involving the above preferred compounds.

DETAILS OF THE INVENTION

The compounds of Formula I can be prepared by one or more of the following methods and variations as described in Schemes 1–9. The definitions of Q, T, W, X, Y, Z, $R^1$ through $R^{11}$, m, n, and p in the compounds of Formulae I–VIII below are as defined above in the Summary of the Invention. Compounds of Formulae Ia and Ib are various subsets of the compounds of Formula I, and all substituents for Formulae Ia and Ib are as defined above for Formula I.

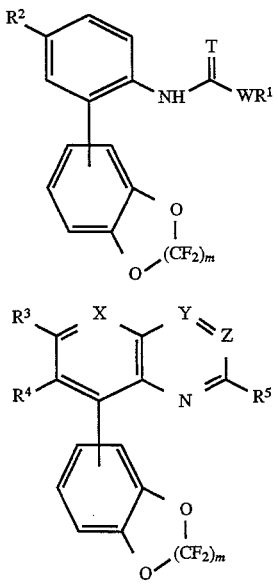

Scheme 1 illustrates the preparation of compounds of Formula I whereby aromatic compounds of Formula II wherein G is chlorine, bromine, iodine, or trifluoromethylsulfonyloxy (OTf) can be coupled with substituted phenyl compounds of Formula III wherein J is a trialkyltin (e.g., Me$_3$Sn), trialkylsilyl (e.g., Me$_3$Si), halometal (e.g., ZnCl, MgBr, CuCl, or HgCl), or boronic acid (e.g., B(OH)$_2$) moiety. The coupling is carried out using methods known in the art: Tsuji, J. *Organic Synthesis with Palladium Compounds;* Springer-Verlag: Berlin, 1980; Negishi, E. *Acc. Chem. Res.* (1982), 15, 340; Stille, J. K. *Angew. Chem.* (1986), 98, 504; Yamamoto, A., Yamagi, A. *Chem. Pharm. Bull.* (1982), 30, 1731 and 2003; Dondoni, A., Fogagnolo, M., Medici, A., Negrini, E. *Synthesis* (1987), 185; Dondoni, A., Fantin, G., Fogagnolo, M., Medici, A., Pedrini, P.  *Synthesis* (1987), 693; Hoshino, Y., Miyaura, N., Suzuki, A. *Bull Chem. Soc. Jpn.* (1988), 61, 3008; Sato, M., Miyaura, N., Suzuki, A. *Chem. Lett* (1989), 1405; Mayaura, N., Yanagi, T., Suzuki, A. *Synth. Commun.* (1981), 11, 513; Siddiqui, M. A., Snieckus, V. *Tetrahedron Lett.* (1988), 29, 5463; Sharp, M. J., Cheng, W., Snieckus, V. *Tetrahedron Lett.* (1987), 28, 5093; Hatanaka, Y., Fukushima, S., Hiyama, T. *Chem. Lett.* (1989), 1711; Bailey, T. R. *Tetrahedron Lett.* (1986), 27, 4407; Echavarren, A. M., Stille, J. K. *J. Am. Chem. Soc.* (1987), 109, 5478; Ali et al., *Tetrahedron Lett.* (1992), 48, 8117; Negishi, E., Takahashi, T., King, A. *Org. Synth* (1987), 66, 67; Negishi, E., King, A., Okukado, N. *J. Org. Chem.* (1977), 42, 1821; and Minato, A., Tamao, K., Huyashi, T., Suzuki, K., Kumada, M. *Tetrahedron Lett.* (1980), 21, 845.

The coupling of II and III is carried out in the presence of a transition metal catalyst such as tetrakis (triphenylphosphine) palladium (0) or bis (triphenylphosphine) palladium (II) dichloride in a solvent such as toluene, acetonitrile, tetrahydrofuran, or ethylene glycol dimethyl ether and optionally in the presence of an aqueous inorganic base such as sodium hydrogen carbonate or an organic base such as triethylamine. As shown in Scheme 1, compounds of Formula I can also be prepared by coupling aromatic compounds of Formula IV wherein J is a trialkyltin (e.g., Me$_3$Sn), trialkylsilyl (e.g., Me$_3$Si), halometal (e.g., ZnCl, MgBr, CuCl, or HgCl), or boronic acid (e.g., B(OH)$_2$) moiety with substituted phenyl compounds of Formula V wherein G is chlorine, bromine, iodine, or trifluoromethylsulfonyloxy (OTf). Compounds of Formula III and V are known in the art. (For m=1, see EP 333,658, and for m=2, see DE 3223505.) The procedure for conducting the coupling is the same as those described and referenced above.

SCHEME 1

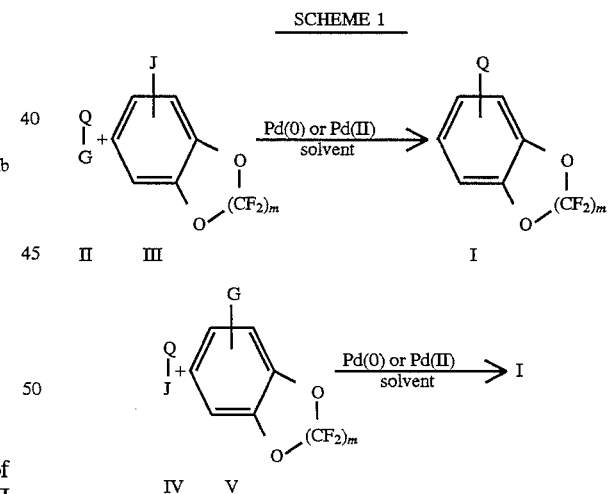

G = Cl, Br, I, OTf
J = SnR$_3$, SiR$_3$, ZnCl, MgBr, CuCl, HgCl, B(OH)$_2$, etc.
R = C$_1$–C$_4$ alkyl By methods also reported in the above cited art, treatment of compounds of Formulae II and V wherein G is hydrogen, bromine or iodine with a metalating agent such as n-butyllithium followed by quenching with a trialkyltin halide, trialkylsilyl halide, metal halide, or trialkyl borate produces intermediates of Formulae III and IV.

Heterocycles of Formula IIb are either known or are readily prepared by procedures and techniques well known in the art, e.g., U.S. Pat. No. 5,389,600 and references therein.

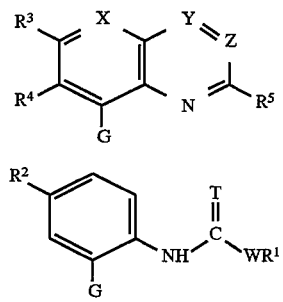

IIb

IIa

In addition, Scheme 2 illustrates the regioselective syntheses of quinoxalines and pyridopyrazines of Formulae VIf and VIg by procedures known in the art, for example: Tenant, G. *J. Chem. Soc.* (1963), 2428–2433 and Ahead, Y. et al. *Tetrahedron* (1965), 21, 861–865. Derivatives of o-nitroacetanilide containing an activated methylene group cyclize in the presence of aqueous base giving compounds of Formula VIc or VId depending on reaction conditions.

Compounds of Formulae VIc and VId can then be reduced to quinoxalines and pyridopyrazines of Formulae VIf and VIg, respectively. N-oxides of Formula VIc can be converted into dihydroxy quinoxalines and pyridopyrazines of Formula VIe. Acid chloride and methyl ester analogs of VIa can also be used in this sequence.

Anilines of Formula VIIb are readily prepared by palladium catalyzed coupling of an ortho-substituted nitrophenyl compound of Formula VII, wherein G is as defined above, with a substituted phenyl compound of Formula III wherein J is as defined above, followed by catalytic or chemical reduction of the nitro group (Scheme 3). Alternatively, the reactivity of the substrates can be reversed; i.e., the coupling is carried out using an ortho-substituted nitrophenyl compound of Formula VIIc and a substituted phenyl compound of Formula V where G and J are as defined above. The procedure for conducting the coupling is the same as those described and referenced above.

Reduction of nitro groups to amino groups is well documented in the chemical literature. See for example, Ohme, R. and Zubek, A. R. and Zubek, A. in *Preparative Organic Chemistry*; Hilgetag, G. and Martini, A., Eds.; John Wiley & Sons, New York, 1972, p 557.

SCHEME 2

SCHEME 3

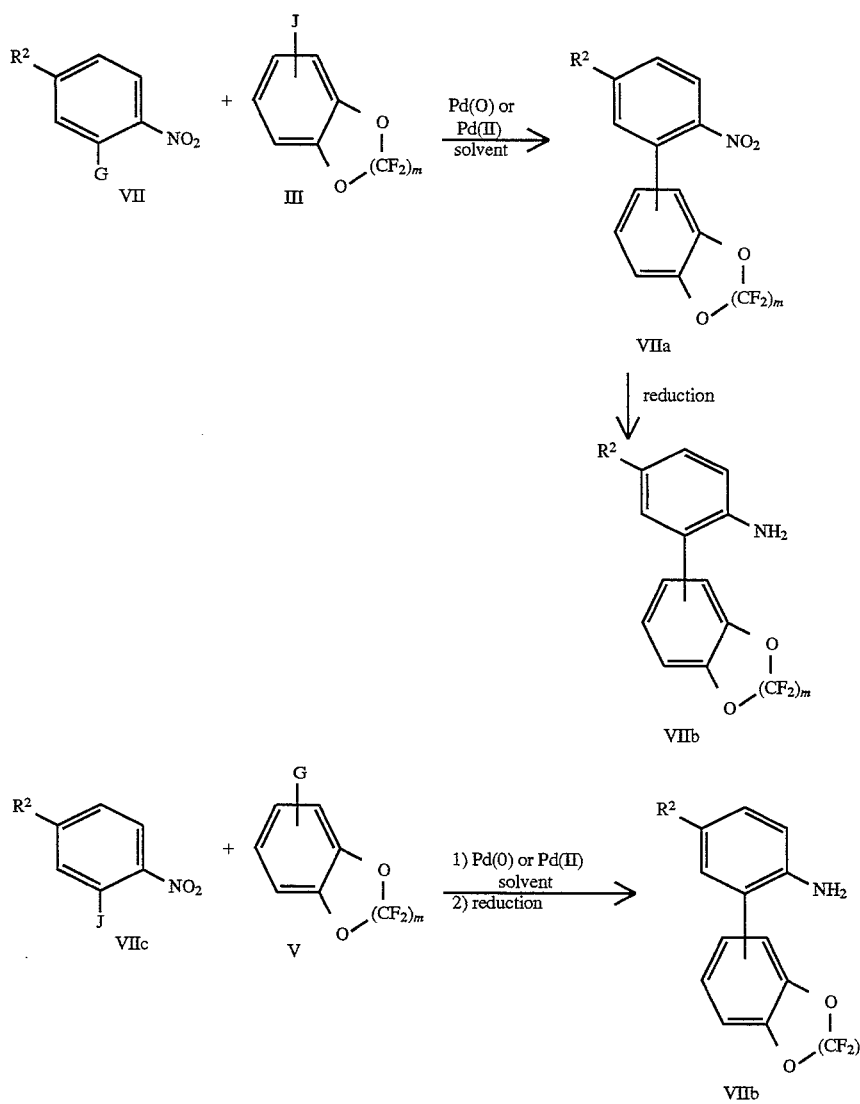

G = Cl, Br, I, OTf
J = SnR₃, SiR₃, ZnCl, MgBr, CuCl, HgCl, B(OH)₂, etc.
R = $C_1$-$C_4$ alkyl In some cases it is desirable to perform the palladium coupling reaction on an N-protected form of the aniline, for example the 2,2-dimethylpropanamide. Upon completion of the coupling reaction, the N-protecting group can be removed, for example by treatment of the 2,2-dimethylpropanamide with acid, to liberate the amino group.

Compounds of Formula Ia can be prepared by one skilled in the art from anilines of Formula VIIb by treatment with an appropriate acyl chloride or acid anhydride (T=O, W=direct bond), chloroformate (T=O, W=O), chlorothiolformate (T=O, W=S), carbamoyl chloride (T=O, W=NR⁶), isothiocyanate (T=S, W=NH), isocyanate (T=O, W=NH), or xanthyl chloride (T=S, W=S), under conditions well known in the literature, for example: Sandler, R. S. and Karo, W. *Organic Functional Group Preparations*, 2nd ed.; Academic: New York. Vol. I, p 274 and Vol. II, pp 152, 260 (Scheme 4).

SCHEME 4

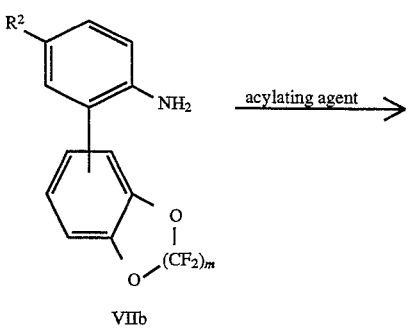

SCHEME 4 -continued

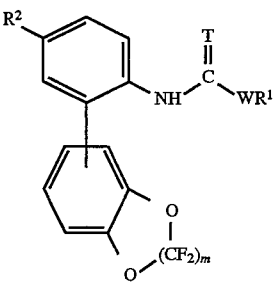

Ia

Anilines of Formula VIIb can also be converted into the corresponding isocyanate by treatment with phosgene or known phosgene equivalents (e.g. ClC(=O)OCCl$_3$), and then condensed with an appropriate alcohol or amine of Formula VIII to afford anilides of Formula Ia (Scheme 5). These techniques are well known in the literature, for example: Sandler, R. S. and Karo, W. *Organic Functional Group Preparations*, 2nd ed.; Academic: New York, Vol. II, pp 152, 260; Lehman, G. and Teichman, H. in *Preparative Organic Chemistry*, 472, Hilgetag, G. and Martini, A., Eds., John Wiley & Sons: New York, 1972; Eckert, H. and Forster, B. *Angew. Chem. Int. Ed. in Engl.*, (1987), 26, 894; Babad, H. and Zeiler, A. G. *Chem. Rev.* (1973), 73, 75.

SCHEME 5

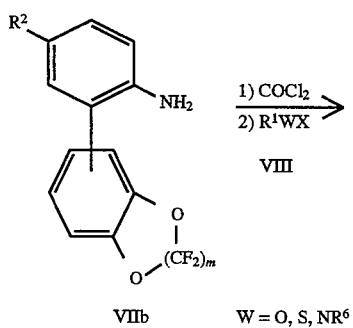

Ia (T = O)

As shown in Scheme 6, compounds of Formula Ia where T=S can be prepared from compounds of Formula Ia where T=O by treatment with P$_2$S$_5$ or Lawesson's reagent (2,4-bis(4-methoxyphenyl)-1,3-dithia-2,4-diphosphetane-2,4-disulfide) under conditions well known in the literature, for example: T. P. Sychera et at., *J. Heterocycl. Chem.* (1989), 26, 1039–1043; E. C. Taylor Jr. et al., *J. Am. Chem. Soc.* (1953), 75, 1904; and O. P. Goel et al., *Synthesis-Stuttgart* (1987), 2, 162–164.

SCHEME 6

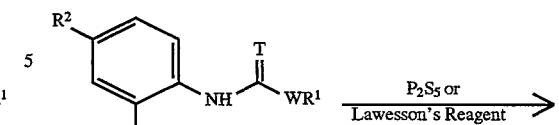

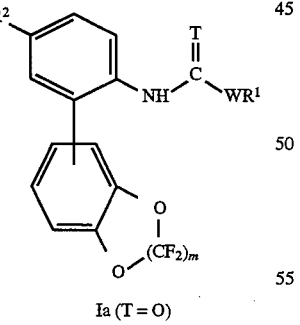

Ia (T = S)

Anilines of Formula VIIb can also be converted into the corresponding isothiocyanate by treatment with thiophosgene or known thiophosgene equivalents (e.g. 1,1'-thiocarbonyldiimidazole) and then condensed with an appropriate alcohol or amine of Formula VIIIa or a Grignard reagent to afford compounds of Formula Ia where T=S (Scheme 7).

SCHEME 7

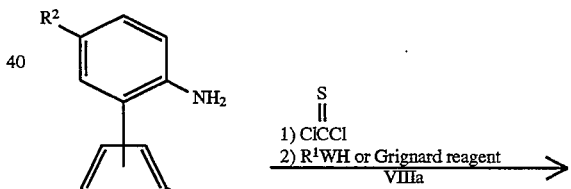

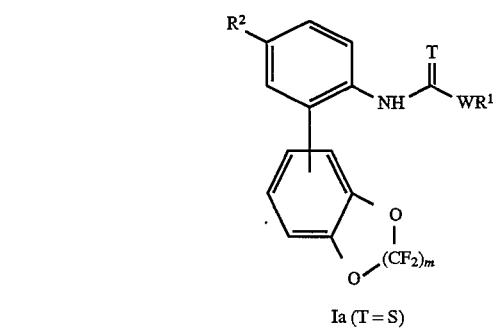

Ia (T = S)

Variation of the substituent R$^2$ on the anilide Q-2 of compounds of Formula Ia may be achieved in one of two ways. First, one skilled in the art may simply select the appropriate aromatic compound of Formula IIa or IV for the palladium coupling in Scheme 1 to give examples with a variety of values for R². In some instances it may be necessary or more convenient to introduce the desired substituents after the coupling reaction was performed. This can be accomplished by electrophilic substitution (Scheme 8) or nucleophilic substitution on compounds of Formula VIIa and/or various functional group transformations (Scheme 9). Methods to perform these transformations are well known in the literature. Some examples include conversion of chloro to bromo (L. J. Street et al., *J. Med. Chem.* (1992), 35, 295–304), bromo to cyano (G. P. Ellis, T. M. Romney-Alexander *Chem. Rev.* (1987), 87, 779–794), bromo to alkoxy and alkylthio, and amino to a variety of substituents via the diazonium salts. Appropriately substituted compounds of Formula VIIa would then be reduced to amino compounds of Formula VIIb using conditions previously discussed.

SCHEME 8

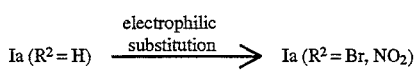

SCHEME 9

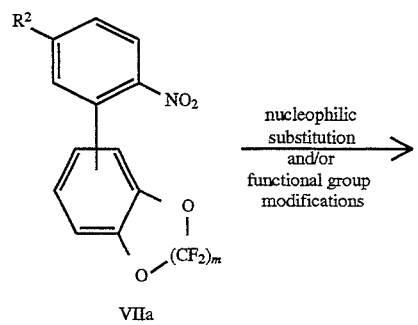

It is recognized that some reagents and reaction conditions described above for preparing compounds of Formula I may not be compatible with certain functionalities present in the intermediates. In these instances, the incorporation of protection/deprotection sequences or functional group interconversions into the synthesis will aid in obtaining the desired products. The use and choice of the protecting groups will be apparent to one skilled in chemical synthesis (see, for example, Greene, T. W.; Wuts, P. G. M. *Protective Groups in Organic Synthesis*, 2nd ed.; Wiley: New York, 1991). One skilled in the art will recognize that, in some cases, after the introduction of a given reagent as it is depicted in any individual scheme, it may be necessary to perform additional routine synthetic steps not described in detail to complete the synthesis of compounds of Formula I.

One skilled in the art will also recognize that compounds of Formula I and the intermediates described herein can be subjected to various electrophilic, nucleophilic, radical, organometallic, oxidation, and reduction reactions to add substituents or modify existing substituents.

Without further elaboration, it is believed that one skilled in the art using the preceding description can utilize the present invention to its fullest extent. The following Examples are, therefore, to be construed as merely illustrative, and not limiting of the disclosure in any way whatsoever. Percentages are by weight unless otherwise indicated. Parts for chromatographic solvent mixtures are by volume unless otherwise indicated. ¹H NMR spectra are reported in ppm downfield from tetramethylsilane; s=singlet, d=doublet, t=triplet, m=multiplet, br s=broad singlet.

EXAMPLE 1

Step A: Preparation of 2-bromo-4-methyl-6-nitrobenzenamine

A solution of bromine (23.24 mL, 453.5 mmol) in glacial acetic acid (50 mL) was added dropwise over 2 h to a mechanically-stirred suspension of 4-methyl-2-nitroaniline (60.00 g, 394.3 mmol) in glacial acetic acid (200 mL) at room temperature under a nitrogen atmosphere. The mixture was stirred at room temperature 1 h, and then most of the acetic acid was removed under reduced pressure. The resultant orange solid was dissolved in a mixture of saturated aqueous sodium bicarbonate (1500 mL) and ethyl acetate (500 mL). The layers were separated and the aqueous solution was again extracted with ethyl acetate. The combined organic layers were washed once with water, dried (MgSO₄), filtered, and concentrated under reduced pressure to afford the title compound of Step A as an orange solid melting at 64°–65.5° C. (89.694 g, 98%). ¹H NMR (CDCl₃): δ2.28 (s,3H), 6.45 (br s,2H), 7.55 (s, 1H), 7.94 (s, 1H).

Step B: Preparation of N-(2-bromo-4-methyl-6-nitrophenyl)-3-oxobutanamide

A solution of diketene (57.71 mL, 748.2 mmol) was added dropwise over 2 h to a stirred solution of title compound of Step A (34.57 g, 149.6 mmol) and 4-dimethylaminopyridine (914 mg, 7.48 mmol) in dry tetrahydrofuran (450 mL) at room temperature under a nitrogen atmosphere. The reaction was allowed to stir at room temperature overnight. First, water was added to the reaction, and then the reaction mixture was poured into water. The mixture was saturated with sodium chloride and was extracted with ethyl acetate three times. The combined organic layers were dried (MgSO₄), filtered, and the solvent was removed under reduced pressure to give a brown oil. The brown oil was suspended in 1-chlorobutane. The resultant precipitate was filtered from this suspension to afford the title compound of Step B as a brown solid melting at 136°–138° C. (21.67 g, 46%). ¹H NMR (CDCl₃): δ2.35 (s,3H), 2.41 (s,3H), 3.63 (s,2H), 7.69 (s,2H), 9.6 (br s, 1H).

Step C: Preparation of 8-bromo-6-methyl-2-quinoxalinol 4-oxide

The title compound of Step B (11.75 g, 37.29 mmol) was suspended in a mixture of isopropanol (120 mL) and water (120 mL) at room temperature under a nitrogen atmosphere. A solution of sodium hydroxide (14.91 g of a 50% aqueous solution, 186.4 mmol) diluted with water (10 mL) was added dropwise to the mixture over 30 min. The mixture was allowed to stir at room temperature overnight. First, 1N hydrochloric acid and then concentrated hydrochloric acid were added dropwise to the reaction mixture until the pH was approximately 2. Solids were filtered from the reaction mixture. These solids were washed with water and then cold ethyl acetate to afford the title compound of Step C as a reddish-brown solid melting at 241°–243° C. (8.67 g, 91%). $^1$H NMR ((CD$_3$)$_2$SO): δ2.47 (s,3H), 7.69 (s, 1H), 7.81 (s, 1H), 8.12 (s, 1H), 8.9 (br s, 1H).

Step D: Preparation of 8-bromo-6-methyl-2-quinoxalinol

The title compound of Step C (25 g, 98 mmol) and sodium dithionite (38 g, 220 mmol) were suspended in a mixture of ethanol (1000 mL) and water (200 mL) at room temperature. After 1 h, most of the solvent was removed under reduced pressure. The residue was diluted with water and acidified with hydrochloric acid. Insolubles were removed by filtration. The filtrate was extracted twice with methylene chloride. The combined organic extracts were dried (MgSO$_4$), filtered, and concentrated under reduced pressure to afford the title compound of Step D as a tan/yellow solid (15.29 g, 65%). $^1$H NMR (CDCl$_3$): δ2.37 (s,3H), 7.5 (d,2H), 8.15 (s, 1H), 9.8 (br s, 1H).

Step E: Preparation of 8-bromo-2-(difluoromethoxy)-6-methylquinoxaline

Tetrabutylammonium bromide (689 mg, 2.14 mmol) and sodium hydroxide (17.1 g of a 50% aqueous solution, 214 mmol) were added to a solution of the title compound of Step D (5.11 g, 21.4 mmol) in dioxane (250 mL) at room temperature. Chlorodifluoromethane was condensed with a cold finger trap and added to the reaction mixture until the mixture was saturated. The reaction mixture was allowed to stir at room temperature overnight. The reaction mixture was slowly poured into water. The resulting mixture was extracted with ethyl acetate three times. The combined organic extracts were dried (MgSO$_4$), filtered, and concentrated under reduced pressure to give a dark-brown oil. Flash chromatography of this brown oil on silica gel, eluting with 1:25 ethyl acetate/hexane afforded the title compound of Step E as a light yellow solid melting at 86°–87° C. (3.23 g, 52%). $^1$H NMR (CDCl$_3$): δ2.57 (s,3H), 7.75 (t, 1H), 7.84 (s, 1H), 7.92 (s, 1H), 8.58 (s, 1H).

Step F: Preparation of (2,2-difluoro-1,3-benzodioxol-4-yl) boronic acid

A solution of n-butyllithium (5.57 mL of a 2.5M solution in hexanes, 13.9 mmol) was added to dry tetrahydrofuran (75 mL) at room temperature under a nitrogen atmosphere. The resulting solution was cooled to −15° C. and N,N,N', N'-tetramethylenediamine (2.10 mL, 13.9 mmol) was added dropwise. The reaction was stirred at −15° C. for 0.5 h and then 2,2-difluoro-1,3-benzodioxole was added dropwise while maintaining the reaction temperature below −10° C. After the addition was complete, the reaction was stirred at −15° C. for 1 h before a solution of trimethylborate (1.58 mL, 13.9 mmol) in dry tetrahydrofuran (5 mL) was added dropwise while maintaining the reaction temperature below −10° C. The reaction mixture was stirred at −10° C. for 1 h and then allowed to come to room temperature while stirring overnight. To the reaction mixture was added a 1N solution of hydrochloric acid and then concentrated hydrochloric acid until the solution was strongly acidic. The acidic solution was poured into water. The resulting mixture was saturated with sodium chloride and extracted with diethyl ether three times. The combined organic extracts were dried (MgSO$_4$), filtered, and concentrated under reduced pressure to give a dark-brown oil. The oil was suspended in boiling petroleum ether and the hot solution filtered to remove a small amount of brown solid. The filtrate was then cooled and filtered to obtain a light-gray solid. The filtrate was concentrated under reduced pressure to give a light-brown solid which was combined with the gray solid obtained from recrystallization to afford the title compound of Step F (1.28 g, 50%). $^1$H NMR (CDCl$_3$): δ4.92 (s,2H), 7.15 (m,2H), 7.5 (d, 1H). $^{19}$F NMR (CDCl$_3$): δ–50.33 (s,2F).

Step G: Preparation of 8-(2,2-difluoro-1,3-benzodioxol-4-yl)-2-(difluoromethoxy)-6-methylquinoxaline To a solution of the title compound of Step E (1.65 g, 5.73 mmol) in ethylene glycol dimethyl ether (25 mL) was added the title compound of Step F (1.73 g, 8.59 mmol), a solution of sodium carbonate (1.82 g, 17.2 mmol) in water (15 mL) and bis(triphenylphosphine) palladium (II) chloride (201 mg, 0.286 mmol). The mixture was heated at reflux overnight, then cooled to room temperature and poured into water. The mixture was extracted twice with ethyl acetate. The combined organic extracts were dried (MgSO$_4$), filtered, and concentrated under reduced pressure to give a dark-brown oil. Flash chromatography of this oil on silica gel eluting with 1:25 ethyl acetate/hexane afforded the title compound of Step G, a compound of the invention, as light-yellow solid melting at 154°–155° C. (525 mg, 25%). $^1$H NMR (CDCl$_3$): δ2.64 (s,3H), 7.15–7.25 (m,3H), 7.39 (t, 1H), 7.7 (s, 1H), 7.97 (s, 1H), 8.62 (s, 1H).

EXAMPLE 2

Step A: Preparation of 5-bromo-2,2-difluoro-1,3-benzodioxole

Iron powder (2.8 g, 50 mmol) was added to a solution of 2,2-difluoro-1,3-benzodioxole (15.8 g, 100 mmol) in carbon tetrachloride (200 mL) at 0° C. under a nitrogen atmosphere. Bromine (5.2 mL, 100 mmol) was then added to the mixture dropwise over 15 min. The reaction was heated to reflux for 1 h and then stirred at room temperature overnight. The mixture was filtered through Celite and the filtrate was washed with 0.1N sodium thiosulfate solution. The organic layer was then dried (MgSO$_4$), filtered, and concentrated under reduced pressure to afford the title compound of Step A as an oil (15.2 g, 64%). $^1$H NMR (CDCl$_3$): δ6.96 (m, 1H), 7.22 (m,2H).

Step B: Preparation of (2,2-difluoro-1,3-benzodioxol-5-yl) boronic acid

A solution of the title compound of Step A (15 g, 63 mmol) in tetrahydrofuran (approximately 200 mL) was cooled to −78° C. under a nitrogen atmosphere. A solution of n-butyllithium (40 mL of a 1.6M solution in hexanes) was added dropwise while maintaining the reaction temperature below −55° C. The reaction mixture was stirred at −78° C. for 20 min before a solution of triisopropylborate (29.4 mL, 127 mmol) in tetrahydrofuran (approximately 50 mL) was added dropwise over 30 min. The reaction was allowed to come to room temperature while stirring for 5 h. The reaction mixture was then partitioned between diethyl ether and 1M hydrochloric acid solution. The organic layer was separated, dried (MgSO$_4$), filtered, and concentrated under reduced pressure to afford the title compound of Step B as a brown oil (15 g) which was used without further purification.

Step C: Preparation of N-[2-(2,2-difluoro-1,3-benzodioxol-5-yl)-4-methylphenyl]acetamide To a mixture of 2-bromo-4-methylacetanilide (1.5 g, 6.6 mmol) and the title compound of Step B (2.0 g, 9.9 mmol) in ethylene glycol dimethyl ether (20 mL) were added a solution of sodium carbonate (2.1 g, 20 mmol) in water (20 mL) and bis(triphenylphosphine) palladium (II) chloride (230 mg, 0.33 mmol). The mixture was heated at reflux overnight, and then additional title compound of Step B (1.0 g, 4.9 mmol) and sodium carbonate (1.0 g, 9.4 mmol) as a solution in water (approximately 10 mL) were added. The mixture was heated at reflux an additional 6 h and then allowed to come to room temperature. The mixture was poured into water and the aqueous mixture was extracted with ethyl acetate four times. The combined organic extracts were dried (MgSO$_4$), filtered and concentrated under reduced pressure to give a dark-brown oil. The oil was purified by flash chromatography on silica gel, eluting with 1:4 ethyl acetate/hexane to afford the title compound of Step C, a compound of the invention, as a light brown solid melting at 105°–107° C. (205 mg, 10%). $^1$H NMR (CD$_3$COCD$_3$): δ1.95 (s,3H), 2.36 (s,3H), 7.2(m,2H), 7.25 (m,3H), 7.8(m, 1H), 8.55(br s, 1H).

EXAMPLE 3

Step A: Preparation of 2-(2,2-difluoro-1,3-benzodioxol-4-yl)-4-methylbenzenamine To a solution of N-[2-(2,2-difluoro- 1,3 -benzodioxol-4-yl)-4-methylphenyl]acetamide (600 mg, 1.97 mmol, prepared according to the procedure for the title compound of Step C of Example 2) in ethanol (10 mL) was added a solution of sodium hydroxide (0.6 mL of a 50% aqueous solution). The resulting mixture was heated to reflux for 3 h and then allowed to stir at room temperature overnight. After an additional 8.5 h at reflux during which time a second portion of sodium hydroxide solution (0.6 mL of a 50% aqueous solution) was added, the reaction was again allowed to stir at room temperature overnight. After another 8 h at reflux, the reaction mixture was cooled to room temperature and the solvent was removed under reduced pressure. The resulting residue was partitioned between water and ethyl acetate, the organic layer was separated, and the aqueous phase was extracted three times with ethyl acetate. The combined organic layers were dried (MgSO$_4$), filtered, and concentrated under reduced pressure to afford the title compound of Step A as a brown liquid (505 mg, 98%). $^1$H NMR (CDCl$_3$): δ2.29 (s,3H), 6.75 (d, 1H), 7.05 (m,3H), 7.15 (m,2H).

Step B: Preparation of N-[2-(2,2-difluoro-1,3-benzodioxol-4-yl)-4-methylphenyl]cyclopropanecarboxamide A solution of the title compound of Step A (500 mg, 1.90 mmol) in dry tetrahydrofuran (10 mL) was cooled in an ice water bath. Triethylamine (592 μL, 3.80 mmol) was added followed by slow addition of cyclopropanecarbonyl chloride (172 μL, 1.90 mmol). The reaction was allowed to come to room temperature while stirring overnight. The reaction mixture was poured into water. The aqueous mixture was saturated with sodium chloride and extracted with ethyl acetate twice. The organic extracts were dried (MgSO$_4$), filtered, and concentrated under reduced pressure to give a beige solid. Flash chromatography of the crude product on silica gel eluting with 1:9 ethyl acetate/hexane afforded the title compound of Step B, a compound of the invention, as a white solid melting at 138°–139° C. (565 mg, 90%). $^1$H NMR (CDCl$_3$): δ0.75 (m,2H), 1.0 (m,2H), 1.3 (m, 1H), 2.37 (s,3H), 7.1 (m,3H), 7.2–7.25 (m,3H), 7.9 (d, 1H).

EXAMPLE 4

Step A: Preparation of N-(2-borono-4-methylphenyl)-2,2-dimethylpropanamide

To a solution of N-(4-methylphenyl)-2,2-dimethylpropanamide (80.0 g, 418 mmol) in 1000 mL of dry tetrahydrofuran (THF) cooled to –78° C. under a nitrogen atmosphere was added a solution of n-butyllithium (502 mL, 1250 mmol of a 2.5M solution in hexanes) over 1 h while maintaining the temperature below –60° C. The reaction mixture was allowed to warm to room temperature overnight.

The reaction mixture was cooled to –5° C. and trimethyl borate (200 mL) was added dropwise over 1 h while maintaining the temperature below 0° C. Stirring was continued while the reaction was allowed to warm to room temperature over 3 h. First, 100 mL of water was added, and then concentrated hydrochloric acid was added dropwise to form a strongly acidic solution. The organic solvents were removed under reduced pressure and then 300 mL of water and 500 mL of diethyl ether were added to form a slurry. The mixture was stirred until a fine, white precipitate developed which was collected by filtration. The solids were washed five times with 200 mL portions of diethyl ether and then twice with 200 mL portions of hexane. The white solid was then suspended in 250 mL of acetone with stirring and 1000 mL of water was added over 40 min. The resulting white precipitate was collected by filtration, washed with water, then with diethyl ether and hexane, and dried in a vacuum oven to afford the title compound of Step A as a white solid melting >270° C. (38.37 g). $^1$H NMR (CDCl$_3$): δ1.07 (s,9H), 2.37 (s,3H), 7.2 (d, 1H), 7.81 (s, 1H), 7.95 (d, 1H), 10.08 (br s,1H).

Step B: Preparation of 4-bromo-2,2-difluoro-1,3-benzodioxole

A solution of 2,2-difluoro-1,3-benzodioxole (2.00 g, 12.6 mmol) in dry tetrahydrofuran (75 mL) was cooled to –78° C. under a nitrogen atmosphere. A solution of n-butyllithium (5.57 mL, 13.9 mmol of a 2.5M solution in hexanes) was added dropwise while maintaining the temperature below –65° C. The reaction mixture was stirred at –78° C. for an additional 30 min after the addition was complete, and then 1,2-dibromotetrafluoroethane (1.66 mL, 13.9 mmol) was added dropwise. After the addition was complete, the reaction mixture was allowed to come to room temperature. After adding a small amount of water to the reaction slowly, the reaction mixture was poured into water and the aqueous mixture was saturated with sodium chloride. This mixture was extracted with diethyl ether. The organic extracts were dried (MgSO$_4$), filtered, and concentrated under reduced pressure to afford the title compound of Step B as a light yellow liquid (2.7 g, 90%). $^1$H NMR (CDCl$_3$): δ7.0 (m, 1H), 7.2 (m,2H). $^{19}$F NMR (CDCl$_3$): δ–49.99 (s,2F).

Step C: Preparation of N-[2-(2,2-difluoro-1,3-benzodioxol-4-yl)-4-methylphenyl]-2,2-dimethylpropanamide To a mixture of the title compound of Step B (10.0 g, 42.2 mmol) and the title compound of Step A (4.96 g, 21.1 mmol) in ethylene glycol dimethyl ether (100 mL) were added a solution of sodium carbonate (4.47 g, 42.2 mmol) in water (25 mL) and bis(triphenylphosphine) palladium (II) chloride (740 mg, 1.05 mmol) at room temperature. The mixture was heated at reflux for 2 h and then allowed to come to room temperature. The solvent was removed under reduced pressure and the residue was suspended in water. The aqueous mixture was extracted with ethyl acetate three times. The organic extracts were dried (MgSO$_4$), filtered, and concentrated under reduced pressure to obtain a brown liquid. Flash chromatography of the crude product on silica gel eluting with 1:6 ethyl acetate/hexane afforded the title compound of Step C, a compound of the invention, as a yellow oily solid (8 g, 55%). $^1$H NMR (CDCl$_3$): δ1.12 (s,9H), 2.37 (s,3H), 7.1 (m,2H), 7.12 (s, 1H), 7.2 (t, 1H), 7.25 (m,1H), 7.3 (br s,1H), 7.9 (d, 1H).

EXAMPLE 5

Step A: Preparation of 5-bromo-2,2,3,3-tetrafluoro-2,3-dihydro-1,4-benzodioxin

A solution of 2,2,3,3-tetrafluoro-2,3-dihydro-1,4-benzodioxin (5.00 g, 24.0 mmol) in dry tetrahydrofuran (150 mL) is cooled to −78° C. under a nitrogen atmosphere. A solution of n-butyllithium (10.6 mL, 26.4 mmol of a 2.5M solution in hexanes) is added dropwise while maintaining the reaction temperature below −65° C. The reaction mixture is stirred at −78° C. for 30 min and then 1,2-dibromotetrafluoroethane (3.16 mL, 26.4 mmol) is added dropwise. After this addition is complete, the reaction mixture is allowed to come to room temperature. A small mount of water is slowly added to the mixture which is then poured into water. The aqueous mixture is saturated with sodium chloride and is extracted with diethyl ether. The combined organic extracts are dried (MgSO₄), filtered, and concentrated under reduced pressure to afford the title compound of Step A.

Step B: Preparation of N-[2-(2,2,3,3-tetrafluoro-2,3-dihydro-1,4-benzodioxin-5-yl)-4-methylphenyl]-2,2-dimethylpropanamide The title compound of Step A of this example (6.00 g, 20.9 mmol), the title compound of Step A in Example 4 (4.91 g, 20.9 mmol), bis(triphenylphospine) palladium (II) chloride (734 mg, 1.05 mmol) and a solution of sodium carbonate (4.43 g, 41.8 mmol) in water (25 mL) are combined in ethylene glycol dimethyl ether (100 mL) at room temperature. The mixture is heated to reflux overnight. The reaction mixture is cooled to room temperature and is poured into water. This mixture is extracted with ethyl acetate. The organic extracts are dried (MgSO₄), filtered, and concentrated under reduced pressure. Flash chromatography of the crude reaction product on silica gel affords the title compound of Step B, a compound of the invention.

By the procedures described herein, the following compounds of Tables 1 to 14 can be prepared. The following abbreviations are used in the Tables which follow: n=normal, Me=methyl, Et=ethyl, nPr=n-propyl, nBu=n-butyl, Ph=phenyl, CN=cyano, and NO₂=nitro.

TABLE 1

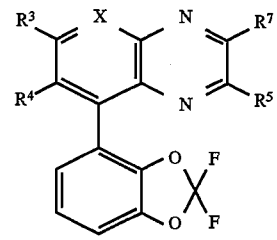

| X | R³ | R⁴ | R⁵ | X | R³ | R⁴ | R⁵ |
|---|---|---|---|---|---|---|---|
| R⁷ = H | | | | | | | |
| CH | Me | H | CF₃ | CH | Me | F | CF₃ |
| CH | Et | H | CF₃ | CH | Me | F | OCHF₂ |
| CH | nPr | H | CF₃ | N | Me | H | CF₃ |
| CH | MeO | H | CF₃ | N | Et | H | CF₃ |
| CH | EtO | H | CF₃ | N | Me | H | OCHF₂ |
| CH | MeS | H | CF₃ | N | Et | H | OCHF₂ |
| CH | EtS | H | CF₃ | CH | Me | H | OCH₂CF₃ |
| CH | MeNH | H | CF₃ | CH | Me | H | CN |
| CH | Me₂N | H | CF₃ | CH | Me | H | CH₃ |
| CH | MeOCH₂ | H | CF₃ | CH | Me | H | Cl |
| CH | MeCH=CH | H | CF₃ | CH | Me | H | SCF₃ |
| CH | HC≡C | H | CF₃ | CH | Me | H | OMe |
| CH | Me | H | OCHF₂ | CH | Me | H | SMe |
| CH | Et | H | OCHF₂ | CH | Me | H | OEt |
| CH | nPr | H | OCHF₂ | CH | Me | H | OCF₂CHF₂ |
| CH | MeO | H | OCHF₂ | CH | Me | H | CH=CHCF₃ |
| CH | EtO | H | OCHF₂ | CH | Me | H | SCHF₂ |
| CH | MeS | H | OCHF₂ | CH | Me | H | SO₂CHF₂ |
| CH | EtS | H | OCHF₂ | CH | Et | H | SCHF₂ |
| CH | MeNH | H | OCHF₂ | N | Me | H | CF₃ |
| CH | Me₂N | H | OCHF₂ | N | Me | H | OCHF₂ |
| CH | MeOCH₂ | H | OCHF₂ | N | Me | F | CF₃ |
| CH | MeCH=CH | H | OCHF₂ | N | Me | F | OCHF₂ |
| CH | HC≡C | H | OCHF₂ | N | Me | H | OMe |
| N | Et | H | CF₃ | CH | nPr | H | SCF₃ |
| N | Et | H | OCHF₂ | CH | MeOCH₂ | H | SCHF₂ |
| CH | CH₃ | H | OCHMe₂ | CH | HC≡C | H | SCF₃ |
| R⁵ = H | | | | | | | |
| CH | Me | H | CF₃ | CH | Me | F | CF₃ |
| CH | Et | H | CF₃ | CH | Me | F | OCHF₂ |
| CH | nPr | H | CF₃ | N | Me | H | CF₃ |
| CH | MeO | H | CF₃ | N | Et | H | CF₃ |

TABLE 1-continued

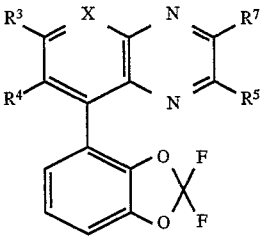

| X | R³ | R⁴ | R⁵ | X | R³ | R⁴ | R⁵ |
|---|---|---|---|---|---|---|---|
| CH | EtO | H | CF₃ | N | Me | H | OCHF₂ |
| CH | MeS | H | CF₃ | N | Et | H | OCHF₂ |
| CH | EtS | H | CF₃ | CH | Me | H | OCH₂CF₃ |
| CH | MeNH | H | CF₃ | CH | Me | H | CN |
| CH | Me₂N | H | CF₃ | CH | Me | H | CH₃ |
| CH | MeOCH₂ | H | CF₃ | CH | Me | H | Cl |
| CH | MeCH=CH | H | CF₃ | CH | Me | H | SCF₃ |
| CH | HC≡C | H | CF₃ | CH | Me | H | OMe |
| CH | Me | H | OCHF₂ | CH | Me | H | SMe |
| CH | Et | H | OCHF₂ | CH | Me | H | OEt |
| CH | nPr | H | OCHF₂ | CH | Me | H | OCF₂CHF₂ |
| CH | MeO | H | OCHF₂ | CH | Me | H | CH=CHCF₃ |
| CH | EtO | H | OCHF₂ | CH | Me | H | SCHF₂ |
| CH | MeS | H | OCHF₂ | CH | Me | H | SO₂CHF₂ |
| CH | EtS | H | OCHF₂ | CH | Et | H | SCHF₂ |
| CH | MeNH | H | OCHF₂ | N | Me | H | CF₃ |
| CH | Me₂N | H | OCHF₂ | N | Me | H | OCHF₂ |
| CH | MeOCH₂ | H | OCHF₂ | N | Me | F | CF₃ |
| CH | MeCH=CH | H | OCHF₂ | N | Me | F | OCHF₂ |
| CH | HC≡C | H | OCHF₂ | N | Me | H | OMe |
| N | Et | H | CF₃ | CH | nPr | H | SCF₃ |
| N | Et | H | OCHF₂ | CH | MeOCH₂ | H | SCHF₂ |
| CH | CH₃ | H | OCHMe₂ | CH | HC≡C | H | SCF₃ |

TABLE 2

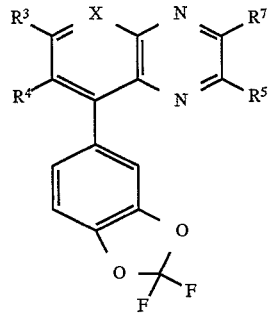

| X | R³ | R⁴ | R⁵ | X | R³ | R⁴ | R⁵ |
|---|---|---|---|---|---|---|---|
| | | | R⁷ = H | | | | |
| CH | Me | H | CF₃ | CH | Me | F | CF₃ |
| CH | Et | H | CF₃ | CH | Me | F | OCHF₂ |
| CH | nPr | H | CF₃ | N | Me | H | CF₃ |
| CH | MeO | H | CF₃ | N | Et | H | CF₃ |
| CH | EtO | H | CF₃ | N | Me | H | OCHF₂ |
| CH | MeS | H | CF₃ | N | Et | H | OCHF₂ |
| CH | EtS | H | CF₃ | CH | Me | H | OCH₂CF₃ |
| CH | MeNH | H | CF₃ | CH | Me | H | CN |
| CH | Me₂N | H | CF₃ | CH | Me | H | CH₃ |
| CH | MeOCH₂ | H | CF₃ | CH | Me | H | Cl |
| CH | MeCH=CH | H | CF₃ | CH | Me | H | SCF₃ |
| CH | HC≡C | H | CF₃ | CH | Me | H | OMe |
| CH | Me | H | OCHF₂ | CH | Me | H | SMe |
| CH | Et | H | OCHF₂ | CH | Me | H | OEt |

TABLE 2-continued

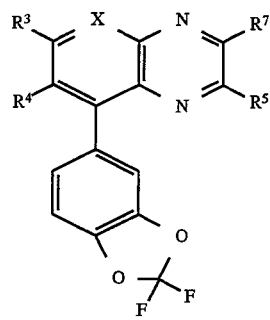

| X | $R^3$ | $R^4$ | $R^5$ | X | $R^3$ | $R^4$ | $R^5$ |
|---|---|---|---|---|---|---|---|
| CH | nPr | H | $OCHF_2$ | CH | Me | H | $OCF_2CHF_2$ |
| CH | MeO | H | $OCHF_2$ | CH | Me | H | $CH=CHCF_3$ |
| CH | EtO | H | $OCHF_2$ | CH | Me | H | $SCHF_2$ |
| CH | MeS | H | $OCHF_2$ | CH | Me | H | $SO_2CHF_2$ |
| CH | EtS | H | $OCHF_2$ | CH | Et | H | $SCHF_2$ |
| CH | MeNH | H | $OCHF_2$ | N | Me | H | $CF_3$ |
| CH | $Me_2N$ | H | $OCHF_2$ | N | Me | H | $OCHF_2$ |
| CH | $MeOCH_2$ | H | $OCHF_2$ | N | Me | F | $CF_3$ |
| CH | MeCH=CH | H | $OCHF_2$ | N | Me | F | $OCHF_2$ |
| CH | HC≡C | H | $OCHF_2$ | N | Me | H | OMe |
| N | Et | H | $CF_3$ | CH | nPr | H | $SCF_3$ |
| N | Et | H | $OCHF_2$ | CH | $MeOCH_2$ | H | $SCHF_2$ |
| CH | $CH_3$ | H | $OCHMe_2$ | CH | HC≡C | H | $SCF_3$ |

$R^5 = H$

| CH | Me | H | $CF_3$ | CH | Me | F | $CF_3$ |
|---|---|---|---|---|---|---|---|
| CH | Et | H | $CF_3$ | CH | Me | F | $OCHF_2$ |
| CH | nPr | H | $CF_3$ | N | Me | H | $CF_3$ |
| CH | MeO | H | $CF_3$ | N | Et | H | $CF_3$ |
| CH | EtO | H | $CF_3$ | N | Me | H | $OCHF_2$ |
| CH | MeS | H | $CF_3$ | N | Et | H | $OCHF_2$ |
| CH | EtS | H | $CF_3$ | CH | Me | H | $OCH_2CF_3$ |
| CH | MeNH | H | $CF_3$ | CH | Me | H | CN |
| CH | $Me_2N$ | H | $CF_3$ | CH | Me | H | $CH_3$ |
| CH | $MeOCH_2$ | H | $CF_3$ | CH | Me | H | Cl |
| CH | MeCH=CH | H | $CF_3$ | CH | Me | H | $SCF_3$ |
| CH | HC≡C | H | $CF_3$ | CH | Me | H | OMe |
| CH | Me | H | $OCHF_2$ | CH | Me | H | SMe |
| CH | Et | H | $OCHF_2$ | CH | Me | H | OEt |
| CH | nPr | H | $OCHF_2$ | CH | Me | H | $OCF_2CHF_2$ |
| CH | MeO | H | $OCHF_2$ | CH | Me | H | $CH=CHCF_3$ |
| CH | EtO | H | $OCHF_2$ | CH | Me | H | $SCHF_2$ |
| CH | MeS | H | $OCHF_2$ | CH | Me | H | $SO_2CHF_2$ |
| CH | EtS | H | $OCHF_2$ | CH | Et | H | $SCHF_2$ |
| CH | MeNH | H | $OCHF_2$ | N | Me | H | $CF_3$ |
| CH | $Me_2N$ | H | $OCHF_2$ | N | Me | H | $OCHF_2$ |
| CH | $MeOCH_2$ | H | $OCHF_2$ | N | Me | F | $CF_3$ |
| CH | MeCH=CH | H | $OCHF_2$ | N | Me | F | $OCHF_2$ |
| CH | HC≡C | H | $OCHF_2$ | N | Me | H | OMe |
| N | Et | H | $CF_3$ | CH | nPr | H | $SCF_3$ |
| N | Et | H | $OCHF_2$ | CH | $MeOCH_2$ | H | $SCHF_2$ |
| CH | $CH_3$ | H | $OCHMe_2$ | CH | HC≡C | H | $SCF_3$ |

TABLE 3

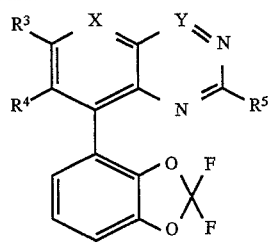

| X | R³ | R⁴ | R⁵ | X | R³ | R⁴ | R⁵ |
|---|----|----|----|---|----|----|----|
| | | | Y = N | | | | |
| CH | Me | H | CF₃ | CH | HC≡C | H | OCHF₂ |
| CH | Et | H | CF₃ | CH | Me | F | CF₃ |
| CH | nPr | H | CF₃ | CH | Me | F | OCHF₂ |
| CH | MeO | H | CF₃ | N | Me | H | CF₃ |
| CH | EtO | H | CF₃ | N | Me | H | OCHF₂ |
| CH | MeS | H | CF₃ | N | Me | H | SCHF₂ |
| CH | EtS | H | CF₃ | N | Me | H | SCF₃ |
| CH | MeNH | H | CF₃ | N | Et | H | OCHF₂ |
| CH | Me₂N | H | CF₃ | CH | Me | H | OCH₂CF₃ |
| CH | MeOCH₂ | H | CF₃ | CH | Me | H | CN |
| CH | MeCH=CH | H | CF₃ | CH | Me | H | CH₃ |
| CH | HC≡C | H | CF₃ | CH | Me | H | Cl |
| CH | Me | H | OCHF₂ | CH | Me | H | OMe |
| CH | Et | H | OCHF₂ | CH | Me | H | SMe |
| CH | nPr | H | OCHF₂ | CH | Me | H | OEt |
| CH | MeO | H | OCHF₂ | CH | Me | H | OCF₂CHF₂ |
| CH | EtO | H | OCHF₂ | CH | Me | H | CH=CHCF₃ |
| CH | MeS | H | OCHF₂ | CH | Me | H | SO₂CHF₂ |
| CH | EtS | H | OCHF₂ | CH | Me | H | OCHMe₂ |
| CH | MeNH | H | OCHF₂ | CH | Et | H | SCF₃ |
| CH | Me₂N | H | OCHF₂ | CH | nPr | H | SCHF₂ |
| CH | MeOCH₂ | H | OCHF₂ | CH | MeOCH₂ | H | SCF₃ |
| CH | MeCH=CH | H | OCHF₂ | CH | HC≡C | H | SCHF₂ |
| | | | Y = CH | | | | |
| CH | Me | H | CF₃ | CH | HC≡C | H | OCHF₂ |
| CH | Et | H | CF₃ | CH | Me | F | CF₃ |
| CH | nPr | H | CF₃ | CH | Me | F | OCHF₂ |
| CH | MeO | H | CF₃ | N | Me | H | CF₃ |
| CH | EtO | H | CF₃ | N | Me | H | OCHF₂ |
| CH | MeS | H | CF₃ | N | Me | H | SCHF₂ |
| CH | EtS | H | CF₃ | N | Me | H | SCF₃ |
| CH | MeNH | H | CF₃ | N | Et | H | OCHF₂ |
| CH | Me₂N | H | CF₃ | CH | Me | H | OCH₂CF₃ |
| CH | MeOCH₂ | H | CF₃ | CH | Me | H | CN |
| CH | CH₂=CH | H | CF₃ | CH | Me | H | CH₃ |
| CH | HC≡C | H | CF₃ | CH | Me | H | Cl |
| CH | Me | H | OCHF₂ | CH | Me | H | OMe |
| CH | Et | H | OCHF₂ | CH | Me | H | SMe |
| CH | nPr | H | OCHF₂ | CH | Me | H | OEt |
| CH | MeO | H | OCHF₂ | CH | Me | H | OCF₂CHF₂ |
| CH | EtO | H | OCHF₂ | CH | Me | H | CH=CHCF₃ |
| CH | MeS | H | OCHF₂ | CH | Me | H | SO₂CHF₂ |
| CH | EtS | H | OCHF₂ | CH | Me | H | OCHMe₂ |
| CH | MeNH | H | OCHF₂ | CH | Et | H | SCF₃ |
| CH | Me₂N | H | OCHF₂ | CH | nPr | H | SCHF₂ |
| CH | MeOCH₂ | H | OCHF₂ | CH | MeOCH₂ | H | SCF₃ |
| CH | CH₂=CH | H | OCHF₂ | CH | HC≡C | H | SCHF₂ |

TABLE 4

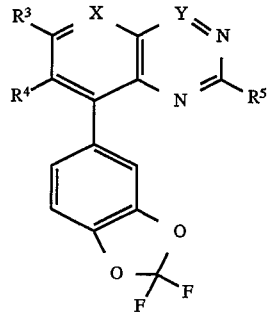

| X | R³ | R⁴ | R⁵ | X | R³ | R⁴ | R⁵ |
|---|----|----|----|---|----|----|----|
| | | | Y = N | | | | |
| CH | Me | H | CF₃ | CH | HC≡C | H | OCHF₂ |
| CH | Et | H | CF₃ | CH | Me | F | CF₃ |
| CH | nPr | H | CF₃ | CH | Me | F | OCHF₂ |
| CH | MeO | H | CF₃ | N | Me | H | CF₃ |
| CH | EtO | H | CF₃ | N | Me | H | OCHF₂ |
| CH | MeS | H | CF₃ | N | Me | H | SCHF₂ |
| CH | EtS | H | CF₃ | N | Me | H | SCF₃ |
| CH | MeNH | H | CF₃ | N | Et | H | OCHF₂ |
| CH | Me₂N | H | CF₃ | CH | Me | H | OCH₂CF₃ |
| CH | MeOCH₂ | H | CF₃ | CH | Me | H | CN |
| CH | MeCH=CH | H | CF₃ | CH | Me | H | CH₃ |
| CH | HC≡C | H | CF₃ | CH | Me | H | Cl |
| CH | Me | H | OCHF₂ | CH | Me | H | OMe |
| CH | Et | H | OCHF₂ | CH | Me | H | SMe |
| CH | nPr | H | OCHF₂ | CH | Me | H | OEt |
| CH | MeO | H | OCHF₂ | CH | Me | H | OCF₂CHF₂ |
| CH | EtO | H | OCHF₂ | CH | Me | H | CH=CHCF₃ |
| CH | MeS | H | OCHF₂ | CH | Me | H | SO₂CHF₂ |
| CH | EtS | H | OCHF₂ | CH | Me | H | OCHMe₂ |
| CH | MeNH | H | OCHF₂ | CH | Et | H | SCF₃ |
| CH | Me₂N | H | OCHF₂ | CH | nPr | H | SCHF₂ |
| CH | MeOCH₂ | H | OCHF₂ | CH | MeOCH₂ | H | SCF₃ |
| CH | MeCH=CH | H | OCHF₂ | CH | HC≡C | H | SCHF₂ |
| | | | Y = CH | | | | |
| CH | Me | H | CF₃ | CH | HC≡C | H | OCHF₂ |
| CH | Et | H | CF₃ | CH | Me | F | CF₃ |
| CH | nPr | H | CF₃ | CH | Me | F | OCHF₂ |
| CH | MeO | H | CF₃ | N | Me | H | CF₃ |
| CH | EtO | H | CF₃ | N | Me | H | OCHF₂ |
| CH | MeS | H | CF₃ | N | Me | H | SCHF₂ |
| CH | EtS | H | CF₃ | N | Me | H | SCF₃ |
| CH | MeNH | H | CF₃ | N | Et | H | OCHF₂ |
| CH | Me₂N | H | CF₃ | CH | Me | H | OCH₂CF₃ |
| CH | MeOCH₂ | H | CF₃ | CH | Me | H | CN |
| CH | MeCH=CH | H | CF₃ | CH | Me | H | CH₃ |
| CH | HC≡C | H | CF₃ | CH | Me | H | Cl |
| CH | Me | H | OCHF₂ | CH | Me | H | OMe |
| CH | Et | H | OCHF₂ | CH | Me | H | SMe |
| CH | nPr | H | OCHF₂ | CH | Me | H | OEt |
| CH | MeO | H | OCHF₂ | CH | Me | H | OCF₂CHF₂ |
| CH | EtO | H | OCHF₂ | CH | Me | H | CH=CHCF₃ |
| CH | MeS | H | OCHF₂ | CH | Me | H | SO₂CHF₂ |
| CH | EtS | H | OCHF₂ | CH | Me | H | OCHMe₂ |
| CH | MeNH | H | OCHF₂ | CH | Et | H | SCF₃ |
| CH | Me₂N | H | OCHF₂ | CH | nPr | H | SCHF₂ |
| CH | MeOCH₂ | H | OCHF₂ | CH | MeOCH₂ | H | SCF₃ |
| CH | CH₂=CH | H | OCHF₂ | CH | HC≡C | H | SCHF₂ |

TABLE 5

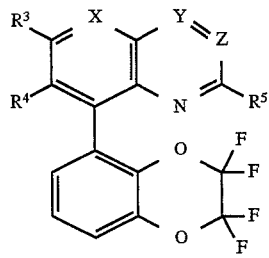

| X | Y | Z | R³ | R⁴ | R⁵ |
|---|---|---|---|---|---|
| CH | N | CH | Me | H | CF₃ |
| CH | N | CH | Me | H | OCHF₂ |
| CH | N | CH | Me | H | SCF₃ |
| CH | N | CH | Me | H | SCHF₂ |
| CH | N | CH | Me | H | OCH₂CF₃ |
| CH | CH | N | Me | H | CF₃ |
| CH | CH | N | Me | H | OCHF₂ |
| CH | CH | N | Me | H | SCF₃ |
| CH | CH | N | Me | H | SCHF₂ |
| CH | CH | N | Me | H | OCH₂CF₃ |
| N | N | CH | Me | H | CF₃ |
| N | N | CH | Me | H | OCHF₂ |
| N | CH | N | Me | H | CF₃ |
| N | CH | N | Me | H | OCHF₂ |
| CH | N | CH | Me | F | OCHF₂ |
| CH | CH | N | Me | F | CF₃ |
| CH | N | CH | Et | H | CF₃ |
| CH | CH | N | Et | H | OCHF₂ |
| CH | N | CH | nPr | H | OCHF₂ |

TABLE 6

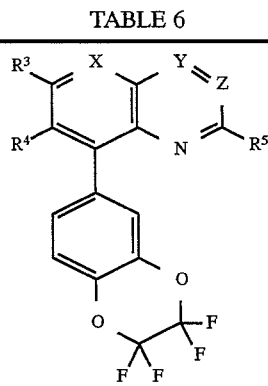

| X | Y | Z | R³ | R⁴ | R⁵ |
|---|---|---|---|---|---|
| CH | N | CH | Me | H | CF₃ |
| CH | N | CH | Me | H | OCHF₂ |
| CH | N | CH | Me | H | SCF₃ |
| CH | N | CH | Me | H | SCHF₂ |
| CH | N | CH | Me | H | OCH₂CF₃ |
| CH | CH | N | Me | H | CF₃ |
| CH | CH | N | Me | H | OCHF₂ |
| CH | CH | N | Me | H | SCF₃ |
| CH | CH | N | Me | H | SCHF₂ |
| CH | CH | N | Me | H | OCH₂CF₃ |
| N | N | CH | Me | H | CF₃ |
| N | N | CH | Me | H | OCHF₂ |
| N | CH | N | Me | H | CF₃ |
| N | CH | N | Me | H | OCHF₂ |
| CH | N | CH | Me | F | OCHF₂ |
| CH | CH | N | Me | F | CF₃ |
| CH | N | CH | Et | H | CF₃ |
| CH | CH | N | Et | H | OCHF₂ |
| CH | N | CH | nPr | H | OCHF₂ |

TABLE 7

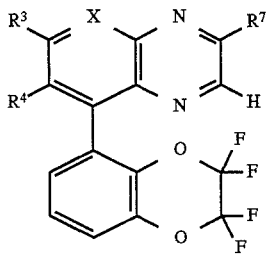

| X | R³ | R⁴ | R⁷ |
|---|---|---|---|
| CH | Me | H | CF₃ |
| CH | Me | H | OCHF₂ |
| CH | Me | H | SCHF₂ |
| CH | Me | F | CF₃ |
| CH | Me | F | OCHF₂ |
| CH | Et | H | CF₃ |
| CH | nPr | H | OCHF₂ |
| N | Me | H | CF₃ |
| N | Me | H | OCHF₂ |
| N | Et | H | OCHF₂ |

TABLE 8

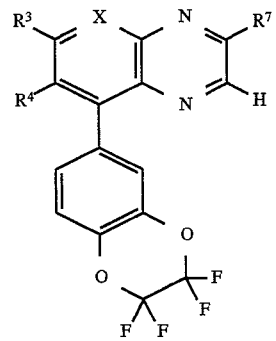

| X | R³ | R⁴ | R⁷ |
|---|---|---|---|
| CH | Me | H | CF₃ |
| CH | Me | H | OCHF₂ |
| CH | Me | H | SCHF₂ |
| CH | Me | F | CF₃ |
| CH | Me | F | OCHF₂ |
| CH | Et | H | CF₃ |
| CH | nPr | H | OCHF₂ |
| N | Me | H | CF₃ |
| N | Me | H | OCHF₂ |
| N | Et | H | OCHF₂ |

TABLE 9

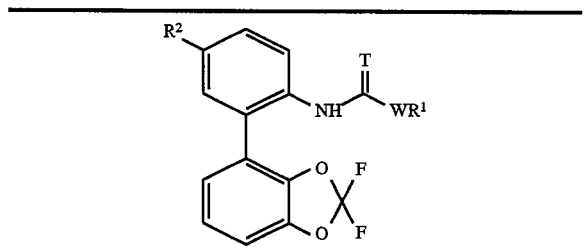

T = O, W is a single bond, R² = Me

| R¹ | R¹ |
|---|---|
| Me | CH(Me)CH₂Cl |
| CH₂F | C(Me)=CHBr |
| CH₂Cl | CH=CHMe |
| CH₂Br | CH(Me)SMe |
| CHF₂ | CH(Me)OMe |
| CHCl₂ | (CH₂)₃Me |
| CF₃ | CH(Me)CH₂Me |
| Et | CH₂CHMe₂ |
| CH₂CF₃ | CMe₃ |
| CH₂CH₂F | cyclobutyl |
| CH₂CH₂Cl | 1-Me-cyclopropyl |
| CH₂CH₂Br | 2-Me-cyclopropyl |
| CHFMe | CH₂-cyclopropyl |
| CHClMe | CH₂C(Me)=CH₂ |
| CHBrMe | CH=CMe₂ |
| CH₂CHF₂ | CHBrCHMe₂ |
| CCl₂Me | CH=C(CH₂Cl)₂ |
| CH₂OMe | C(Me)₂CH₂Cl |
| CH₂SMe | C(Me)₂OMe |
| CH₂CF₃ | C(Me)₂SMe |
| (CH₂)₂Me | (CH₂)₄Me |
| CHMe₂ | CH(CH₂CH₃)₂ |
| cyclopropyl | Ph |
| C(Me)=CH₂ | CMe₂Br |

T = O, R² = Me

| W | R¹ | W | R¹ |
|---|---|---|---|
| O | Me | S | CH₂CHMe₂ |
| O | Et | NH | Me |
| O | nPr | NH | Et |
| O | nBu | NH | nPr |
| O | CHMe₂ | NH | nBu |
| O | CH₂CH=CH₂ | NH | CHMe₂ |
| O | CH₂CHMe₂ | NH | CH₂CHMe₂ |
| S | Me | NMe | Me |
| S | Et | NMe | Et |
| S | nPr | NMe | nPr |
| S | CHMe₂ | NOMe | Me |

T = S, W is a single bond

| R¹ | R² | R¹ | R² |
|---|---|---|---|
| Me | Me | CHMe₂ | Cl |
| Et | Me | CH₂CHMe₂ | Br |
| nPr | Me | cyclopropyl | Et |
| CF₃ | Me | CHMe₂ | OMe |
| CHMe₂ | Me | CH₂CHMe₂ | OEt |
| CH₂CHMe₂ | Me | CHMe₂ | CN |
| CMe₃ | Me | CMe₃ | NO₂ |
| cyclopropyl | Me | CMe₃ | NHMe |
| cyclobutyl | Me | CMe₃ | NMe₂ |
| Ph | Me | cyclopropyl | Br |
| CH₂CF₃ | Me | CMe₃ | Et |
| CH=CMe₂ | Me | CH₂CHMe₂ | CN |
| 1-Me-cyclopropyl | Me | CHMe₂ | NEt₂ |
| CHMe₂ | H | CH₂CHMe₂ | H |

TABLE 10

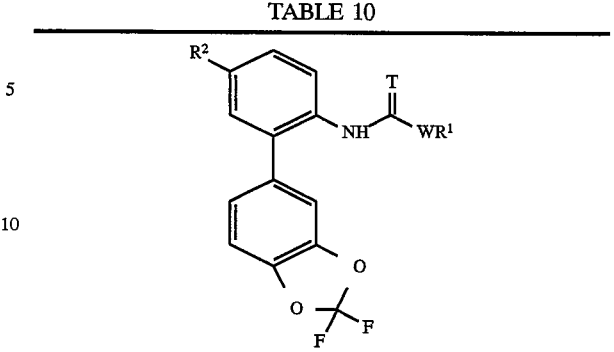

T = O, W is a single bond, R² = Me

| R¹ | R¹ |
|---|---|
| Me | CH(Me)CH₂Cl |
| CH₂F | C(Me)=CHBr |
| CH₂Cl | CH=CHMe |
| CH₂Br | CH(Me)SMe |
| CHF₂ | CH(Me)OMe |
| CHCl₂ | (CH₂)₃Me |
| CF₃ | CH(Me)CH₂Me |
| Et | CH₂CHMe₂ |
| CH₂CF₃ | CMe₃ |
| CH₂CH₂F | cyclobutyl |
| CH₂CH₂Cl | 1-Me-cyclopropyl |
| CH₂CH₂Br | 2-Me-cyclopropyl |
| CHFMe | CH₂-cyclopropyl |
| CHClMe | CH₂C(Me)=CH₂ |
| CHBrMe | CH=CMe₂ |
| CH₂CHF₂ | CHBrCHMe₂ |
| CCl₂Me | CH=C(CH₂Cl)₂ |
| CH₂OMe | C(Me)₂CH₂Cl |
| CH₂SMe | C(Me)₂OMe |
| CH₂CF₃ | C(Me)₂SMe |
| (CH₂)₂Me | (CH₂)₄Me |
| CHMe₂ | CH(CH₂CH₃)₂ |
| cyclopropyl | Ph |
| C(Me)=CH₂ | CMe₂Br |

T = O, R² = Me

| W | R¹ | W | R¹ |
|---|---|---|---|
| O | Me | S | CH₂CHMe₂ |
| O | Et | NH | Me |
| O | nPr | NH | Et |
| O | nBu | NH | nPr |
| O | CHMe₂ | NH | nBu |
| O | CH₂CH=CH₂ | NH | CHMe₂ |
| O | CH₂CHMe₂ | NH | CH₂CHMe₂ |
| S | Me | NMe | Me |
| S | Et | NMe | Et |
| S | nPr | NMe | nPr |
| S | CHMe₂ | NOMe | Me |

T = S, W is a single bond

| R¹ | R² | R¹ | R² |
|---|---|---|---|
| Me | Me | CHMe₂ | Cl |
| Et | Me | CH₂CHMe₂ | Br |
| nPr | Me | cyclopropyl | Et |
| CF₃ | Me | CHMe₂ | OMe |
| CHMe₂ | Me | CH₂CHMe₂ | OEt |
| CH₂CHMe₂ | Me | CHMe₂ | CN |
| CMe₃ | Me | CMe₃ | NO₂ |
| cyclopropyl | Me | CMe₃ | NHMe |
| cyclobutyl | Me | CMe₃ | NMe₂ |
| Ph | Me | cyclopropyl | Br |
| CH₂CF₃ | Me | CMe₃ | Et |
| CH=CMe₂ | Me | CH₂CHMe₂ | CN |
| 1-Me-cyclopropyl | Me | CHMe₂ | NEt₂ |

TABLE 10-continued

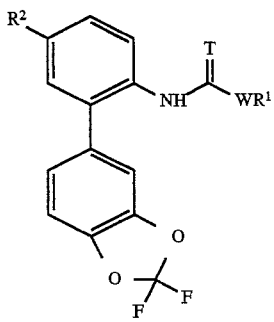

| WR¹ | R² | WR¹ | R² |
|---|---|---|---|
| CHMe₂ | H | CH₂CHMe₂ | H |

TABLE 11

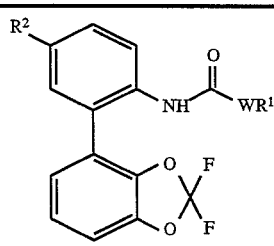

| WR¹ | R² | WR¹ | R² |
|---|---|---|---|
| Me | H | Me | Br |
| Et | H | Et | Br |
| nPr | H | nPr | Br |
| CHMe₂ | H | CHMe₂ | Br |
| cyclopropyl | H | cyclopropyl | Br |
| cyclobutyl | H | cyclobutyl | Br |
| 1-Me-cyclopropyl | H | 1-Me-cyclopropyl | Br |
| 2-Me-cyclopropyl | H | 2-Me-cyclopropyl | Br |
| CMe₃ | H | CMe₃ | Br |
| CF₃ | H | CF₃ | Br |
| CH₂CF₃ | H | CH₂CF₃ | Br |
| CHF₂ | H | CHF₂ | Br |
| C(Me)=CH₂ | H | C(Me)=CH₂ | Br |
| CH₂OMe | H | OCHMe₂ | Br |
| CHMe₂ | Cl | CHMe₂ | NO₂ |
| CH₂CHMe₂ | Cl | CH₂CHMe₂ | NO₂ |
| cyclopropyl | Cl | cyclopropyl | NO₂ |
| CMe₃ | Cl | CMe₃ | NO₂ |
| CF₃ | Cl | CF₃ | NO₂ |
| OCHMe₂ | Cl | OCHMe₂ | NO₂ |
| CHMe₂ | Et | cyclopropyl | CN |
| CH₂CHMe₂ | Et | CMe₂ | CN |
| OCHMe₂ | Et | Me | CN |
| cyclopropyl | Et | cyclobutyl | CN |
| CMe₃ | Et | CHMe₂ | CN |
| Me | Et | CH₂CHMe₂ | CN |
| CMe₃ | OMe | CMe₃ | NHMe |
| Me | OMe | Et | NHMe |
| CHMe₂ | OMe | CHMe₂ | NMe₂ |
| CH₂CHMe₂ | OMe | CH₂CHMe₂ | NMe₂ |
| cyclopropyl | OMe | cyclopropyl | NHEt |
| OCHMe₂ | OMe | CHMe₂ | SMe |
| CH₂CF₃ | OEt | CH₂CHMe₂ | SEt |
| CHMe₂ | OEt | cyclopropyl | CH₂OMe |
| CH₂CHMe₂ | NEt₂ | CHMe₂ | CH₂SMe |
| SCHMe₂ | Et | CH₂CF₃ | OMe |
| NMe₂ | Et | SMe | NO₂ |
| CH₂OMe | Et | OCHMe₂ | NMe₂ |
| C(Me)=CH | CN | C(Me)=CH | CH₂OMe |
| CH₂OMe | Br | NMe₂ | CH₂SMe |

TABLE 12

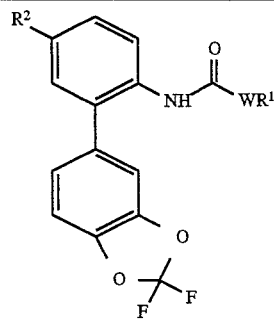

| WR¹ | R² | WR¹ | R² |
|---|---|---|---|
| Me | H | Me | Br |
| Et | H | Et | Br |
| nPr | H | nPr | Br |
| CHMe₂ | H | CHMe₂ | Br |
| cyclopropyl | H | cyclopropyl | Br |
| cyclobutyl | H | cyclobutyl | Br |
| 1-Me-cyclopropyl | H | 1-Me-cyclopropyl | Br |
| 2-Me-cyclopropyl | H | 2-Me-cyclopropyl | Br |
| CMe₃ | H | CMe₃ | Br |
| CF₃ | H | CF₃ | Br |
| CH₂CF₃ | H | CH₂CF₃ | Br |
| CHF₂ | H | CHF₂ | Br |
| C(Me)=CH₂ | H | C(Me)=CH₂ | Br |
| CH₂OMe | H | OCHMe₂ | Br |
| CHMe₂ | Cl | CHMe₂ | NO₂ |
| CH₂CHMe₂ | Cl | CH₂CHMe₂ | NO₂ |
| cyclopropyl | Cl | cyclopropyl | NO₂ |
| CMe₃ | Cl | CMe₃ | NO₂ |
| CF₃ | Cl | CF₃ | NO₂ |
| OCHMe₂ | Cl | OCHMe₂ | NO₂ |
| CHMe₂ | Et | cyclopropyl | CN |
| CH₂CHMe₂ | Et | CMe₂ | CN |
| OCHMe₂ | Et | Me | CN |
| cyclopropyl | Et | cyclobutyl | CN |
| CMe₃ | Et | CHMe₂ | CN |
| Me | Et | CH₂CHMe₂ | CN |
| CMe₃ | OMe | CMe₃ | NHMe |
| Me | OMe | Et | NHMe |
| CHMe₂ | OMe | CHMe₂ | NMe₂ |
| CH₂CHMe₂ | OMe | CH₂CHMe₂ | NMe₂ |
| cyclopropyl | OMe | cyclopropyl | NHEt |
| OCHMe₂ | OMe | CHMe₂ | SMe |
| CH₂CF₃ | OEt | CH₂CHMe₂ | SEt |
| CHMe₂ | OEt | cyclopropyl | CH₂OMe |
| CH₂CHMe₂ | NEt₂ | CHMe₂ | CH₂SMe |
| SCHMe₂ | Et | CH₂CF₃ | OMe |
| NMe₂ | Et | SMe | NO₂ |
| CH₂OMe | Et | OCHMe₂ | NMe₂ |
| C(Me)=CH | CN | C(Me)=CH | CH₂OMe |
| CH₂OMe | Br | NMe₂ | CH₂SMe |

TABLE 13

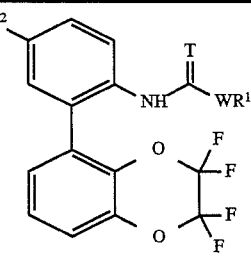

| T | R² | WR¹ | T | R² | WR¹ |
|---|---|---|---|---|---|
| O | Me | CMe₃ | O | Me | SCHMe₂ |
| O | Me | Me | O | Me | NMe₂ |

TABLE 13-continued

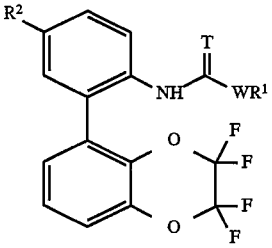

| T | $R^2$ | $WR^1$ | T | $R^2$ | $WR^1$ |
|---|---|---|---|---|---|
| O | Me | $CHMe_2$ | O | Me | $CF_3$ |
| O | Me | $CH_2CHMe_2$ | O | Br | $CHMe_2$ |
| O | Me | cyclopropyl | O | Cl | $CH_2CHMe_2$ |
| O | Me | $OCHMe_2$ | O | Et | cyclopropyl |
| S | Me | $CH_2CHMe_2$ | O | CN | $CHMe_2$ |
| O | $NMe_2$ | $CHMe_2$ | O | $NO_2$ | $CH_2CHMe_2$ |

TABLE 14

| T | $R^2$ | $WR^1$ | T | $R^2$ | $WR^1$ |
|---|---|---|---|---|---|
| O | Me | $CMe_3$ | O | Me | $SCHMe_2$ |
| O | Me | Me | O | Me | $NMe_2$ |
| O | Me | $CHMe_2$ | O | Me | $CF_3$ |
| O | Me | $CH_2CHMe_2$ | O | Br | $CHMe_2$ |
| O | Me | cyclopropyl | O | Cl | $CH_2CHMe_2$ |
| O | Me | $OCHMe_2$ | O | Et | cyclopropyl |
| S | Me | $CH_2CHMe_2$ | O | CN | $CHMe_2$ |
| O | $NMe_2$ | $CHMe_2$ | O | $NO_2$ | $CH_2CHMe_2$ |

Formulation/Utility

Compounds of this invention will generally be used as a formulation or composition with an agriculturally suitable carrier comprising at least one of a liquid diluent, a solid diluent or a surfactant. The formulation or composition ingredients are selected to be consistent with the physical properties of the active ingredient, mode of application and environmental factors such as soil type, moisture and temperature. Useful formulations include liquids such as solutions (including emulsifiable concentrates), suspensions, emulsions (including microemulsions and/or suspoemulsions) and the like which optionally can be thickened into gels. Useful formulations further include solids such as dusts, powders, granules, pellets, tablets, films, and the like which can be water-dispersible ("wettable") or water-soluble. Active ingredient can be (micro)encapsulated and further formed into a suspension or solid formulation; alternatively the entire formulation of active ingredient can be encapsulated (or "overcoated"). Encapsulation can control or delay release of the active ingredient. Sprayable formulations can be extended in suitable media and used at spray volumes from about one to several hundred liters per hectare. High-strength compositions are primarily used as intermediates for further formulation.

The formulations will typically contain effective amounts of active ingredient, diluent and surfactant within the following approximate ranges which add up to 100 percent by weight.

| | Weight Percent | | |
|---|---|---|---|
| | Active Ingredient | Diluent | Surfactant |
| Water-Dispersible and Water-soluble Granules, Tablets and Powders. | 5–90 | 0–94 | 1–15 |
| Suspensions, Emulsions, Solutions (including Emulsifiable Concentrates) | 5–50 | 40–95 | 0–15 |
| Dusts | 1–25 | 70–99 | 0–5 |
| Granules and Pellets | 0.01–99 | 5–99.99 | 0–15 |
| High Strength Compositions | 90–99 | 0–10 | 0–2 |

Typical solid diluents are described in Watkins, et al., *Handbook of Insecticide Dust Diluents and Carriers*, 2nd Ed., Dorland Books, Caldwell, N.J. Typical liquid diluents are described in Marsden, *Solvents Guide*, 2nd Ed., Interscience, N.Y., 1950. *McCutcheon's Detergents and Emulsifiers Annual*, Allured Publ. Corp., Ridgewood, N.J., as well as Sisely and Wood, *Encyclopedia of Surface Active Agents*, Chemical Publ. Co., Inc., New York, 1964, list surfactants and recommended uses. All formulations can contain minor amounts of additives to reduce foam, caking, corrosion, microbiological growth and the like, or thickeners to increase viscosity.

Surfactants include, for example, polyethoxylated alcohols, polyethoxylated alkylphenols, polyethoxylated sorbitan fatty acid esters, dialkyl sulfosuccinates, alkyl sulfates, alkylbenzene sulfonates, organosilicones, N,N-dialkyltaurates, lignin sulfonates, naphthalene sulfonate formaldehyde condensates, polycarboxylates, and polyoxyethylene/polyoxypropylene block copolymers. Solid diluents include, for example, clays such as bentonite, montmorillinite, attapulgite and kaolin, starch, sugar, silica, talc, diatomaceous earth, urea, calcium carbonate, sodium carbonate and bicarbonate, and sodium sulfate. Liquid diluents include, for example, water, N,N-dimethylformamide, dimethyl sulfoxide, N-alkylpyrrolidone, ethylene glycol, polypropylene glycol, paraffins, alkylbenzenes, alkylnaphthalenes, oils of olive, castor, linseed, tung, sesame, corn, peanut, cotton-seed, soybean, rape-seed and coconut, fatty acid esters, ketones such as cyclohexanone, 2-heptanone, isophorone and 4-hydroxy-4-methyl-2-pentanone, and alcohols such as methanol, cyclohexanol, decanol and tetrahydrofurfuryl alcohol.

Solutions, including emulsifiable concentrates, can be prepared by simply mixing the ingredients. Dusts and powders can be prepared by blending and, usually, grinding as in a hammer mill or fluid-energy mill. Suspensions are usually prepared by wet-milling; see, for example, U.S. Pat. No. 3,060,084. Granules and pellets can be prepared by spraying the active material upon preformed granular carriers or by agglomeration techniques. See Browning, "Agglomeration", *Chemical Engineering*, Dec. 4, 1967, pp 147–48, *Perry's Chemical Engineer's Handbook*, 4th Ed., McGraw-Hill, New York, 1963, pages 8–57 and following, and WO 91/13546. Pellets can be prepared as described in U.S. Pat. No. 4,172,714. Water-dispersible and water-soluble granules can be prepared as taught in U.S. Pat. No. 4,144,050, U.S.

Pat. No. 3,920,442 and DE 3,246,493. Tablets can be prepared as taught in U.S. Pat. No. 5,180,587, U.S. Pat. No. 5,232,701 and U.S. Pat. No. 5,208,030. Films can be prepared as taught in GB 2,095,558 and U.S. Pat. No. 3,299,566.

For further information regarding the art of formulation, see U.S. Pat. No. 3,235,361, Col. 6, line 16 through Col. 7, line 19 and Examples 10–41; U.S. Pat. No. 3,309,192, Col. 5, line 43 through Col. 7, line 62 and Examples 8, 12, 15, 39, 41, 52, 53, 58, 132, 138–140, 162–164, 166, 167 and 169–182; U.S. Pat. No. 2,891,855, Col. 3, line 66 through Col. 5, line 17 and Examples 1–4; Klingman, *Weed Control as a Science*, John Wiley and Sons, Inc., New York, 1961, pp 81–96; and Hance et al., *Weed Control Handbook*, 8th Ed., Blackwell Scientific Publications, Oxford, 1989.

In the following Examples, all percentages are by weight and all formulations are prepared in conventional ways. Compound numbers refer to compounds in Index Tables A–C.

| Example A<br>High Strength Concentrate | |
|---|---|
| Compound 3 | 98.5% |
| silica aerogel | 0.5% |
| synthetic amorphous fine silica | 1.0%. |
| Example B<br>Wettable Powder | |
| Compound 11 | 65.0% |
| dodecylphenol polyethylene glycol ether | 2.0% |
| sodium ligninsulfonate | 4.0% |
| sodium silicoaluminate | 6.0% |
| montmorillonite (calcined) | 23.0%. |
| Example C<br>Granule | |
| Compound 3 | 10.0% |
| attapulgite granules (low volatile matter, 0.71/0.30 mm; U.S.S. No. 25–50 sieves) | 90.0%. |
| Example D<br>Extruded Pellet | |
| Compound 11 | 25.0% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0%. |

Tests results indicate that the compounds of the present invention are highly active preemergent and/or postemergent herbicides and/or plant growth regulants. Many of them have utility for broad-spectrum pre- and/or postemergence weed control in areas where complete control of all vegetation is desired such as around fuel storage tanks, industrial storage areas, parking lots, drive-in theaters, around billboards and highway and railroad structures. Some of the compounds are useful for the control of selected grass and broadleaf weeds with tolerance to important agronomic crops which include but are not limited to barley, cotton, wheat, rape, sugarbeets, corn, soybeans, rice, and plantation crops including coffee, cocoa, oil palm, rubber, sugarcane, citrus, grapes, fruit trees, nut trees, banana, plantain, pineapple, conifers, e.g., loblolly pine, and turf species, e.g., Kentucky bluegrass, St. Augustine grass, Kentucky fescue and bermudagrass. Those skilled in the art will appreciate that not all compounds are equally effective against all weeds. Alternatively, the subject compounds are useful to modify plant growth.

Compounds of this invention can be used alone or in combination with other commercial herbicides, insecticides or fungicides. A mixture of one or more of the following herbicides with a compound of this invention may be particularly useful for weed control: acetochlor, acifluorfen and its sodium salt, acrolein (2-propenal), alachlor, ametryn, amidosulfuron, amitrole, ammonium sulfamate, anilofos, asulam, atrazine, azimsulfuron, benazolin, benazolin-ethyl, benfluralin, benfuresate, bensulfuron-methyl, bensulide, bentazone, bifenox, bromacil, bromoxynil, bromoxynil octanoate, butachlor, butralin, butylate, chlomethoxyfen, chloramben, chlorbromuron, chloridazon, chlorimuron-ethyl, chlomitrofen, chlorotoluron, chlorpropham, chlorsulfuron, chlorthal-dimethyl, cinmethylin, cinosulfuron, clethodim, clomazone, clopyralid, clopyralid-olamine, cyanazine, cycloate, cyclosulfamuron, 2,4-D and its butotyl, butyl, isoctyl and isopropyl esters and its dimethylammonium, diolamine and trolamine salts, daimuron, dalapon, dalapon-sodium, dazomet, 2,4-DB and its dimethylammonium, potassium and sodium salts, desmedipham, desmetryn, dicamba and its dimethylammonium, potassium and sodium salts, dichlobenil, dichlorprop, diclofop-methyl, difenzoquat metilsulfate, diflufenican, dimepiperate, dimethylarsinic acid and its sodium salt, dinitramine, diphenamid, diquat dibromide, dithiopyr, diuron, DNOC, endothal, EPTC, esprocarb, ethalfluralin, ethametsulfuron-methyl, ethofumesate, ethyl α,2-dichloro-5-[4-(difluoromethyl)-4,5-dihydro-3-methyl-5-oxo-1H-1,2,4-triazol-1-yl]-4-fluorobenzenepropanoate (F8426), fenoxaprop-ethyl, fenoxaprop-P-ethyl, fenuron, fenuron-TCA, flareprop-methyl, flamprop-M-isopropyl, flamprop-M-methyl, flazasulfuron, fluazifop-butyl, fluazifop-P-butyl, fluchloralin, flumetsulam, flumiclorac-pentyl, flumioxazin, fluometuron, fluoroglycofen-ethyl, flupoxam, fluridone, flurochloridone, fluroxypyr, fomesafen, fosamine-ammonium, glufosinate, glufosinate-ammonium, glyphosate, glyphosate-isopropylammonium, glyphosate-sesquisodium, glyphosate-trimesium, halosulfuron-methyl, haloxyfop-etotyl, haloxyfop-methyl, hexazinone, imazamethabenz-methyl, imazapyr, imazaquin, imazaquin-ammonium, imazethapyr, imazethapyr-ammonium, imazosulfuron, ioxynil, ioxynil octanoate, ioxynil-sodium, isoproturon, isouron, isoxaben, lactofen, lenacil, linuron, maleic hydrazide, MCPA and its dimethylammonium, potassium and sodium salts, MCPA-isoctyl, mecoprop, mecoprop-P, mefenacet, mefluidide, metam-sodium, methabenzthiazuron, methyl [[2-chloro-4-fluoro-5-[(tetrahydro-3-oxo- 1H,3H-[1,3,4]thiadiazolo[3,4-α] pyridazin-1-ylidene)amino]phenyl]thioacetate (KIH 9201), methylarsonic acid and its calcium, monoammonium, monosodium and disodium salts, methyl [[[1-[5-[2-chloro-4-(trifluoromethyl)phenoxy]-2-nitrophenyl]-2-methoxyethylidene]amino]oxy]acetate (AKH-7088), methyl 5-[[[[(4,6-dimethyl-2-pyrimidinyl) amino]carbonyl]amino]sulfonyl]-1-(2-pyridinyl)-1H-pyrazole-4-carboxylate (NC-330), metobenzuron, metolachlor, metoxuron, metribuzin, metsulfuron-methyl, molinate, monolinuron, napropamide, naptalarn, neburon, nicosulfuron, norflurazon, oryzalin, oxadiazon, oxyfluorfen, paraquat dichloride, pebulate, pendimethalin, perfluidone, phenmedipham, picloram, picloram-potassium, pretilachlor, primisulfuron-methyl, prometon, prometryn, propachlor, propanil, propazine, propham, propyzamide, prosulfuron, pyrazolynate, pyrazosulfuron-ethyl, quinclorac, quizalofop-ethyl, quizalofop-P-ethyl, quizalofop-P-tefuryl, rimsulfuron, sethoxydim, siduron, simazine, sulcotrione (ICIA0051), sulfentrazone, sulfometuron-methyl, TCA, TCA-sodium, tebuthiuron, terbacil, terbuthylazine, terbutryn, thenylchlor, thifensulfuron-methyl, thiobencarb, tralkoxydim, tri-allate, triasulfuron, tribenuron-methyl, triclopyr, triclopyr-butotyl, triclopyr-triethylammonium, tridiphane, trifluralin, triflusulfuron-methyl, and vernolate.

In certain instances, combinations with other herbicides having a similar spectrum of control but a different mode of action will be particularly advantageous for preventing the development of resistant weeds.

A herbicidally effective amount of the compounds of this invention is determined by a number of factors. These factors include: formulation selected, method of application, amount and type of vegetation present, growing conditions, etc. In general, a herbicidally effective amount of a compound(s) of this invention is 0.001 to 20 kg/ha with a preferred range of 0.004 to 1.0 kg/ha. One skilled in the art can easily determine the herbicidally effective amount necessary for the desired level of weed control.

The following Tests demonstrate the control efficacy of the compounds of this invention against specific weeds. The weed control afforded by the compounds is not limited, however, to these species. See Index Tables A–C for compound descriptions.

INDEX TABLE A

| Cmpd No. | T | W | R¹ | R² | m | mp (°C.) |
|---|---|---|---|---|---|---|
| 1 | O | bond | CH₃ | CH₃ | 1 | 113–115 |
| 2 (Ex. 4) | O | bond | C(CH₃)₃ | CH₃ | 1 | 89–90 |
| 3 | O | bond | CH(CH₃)₂ | CH₃ | 1 | 143–144 |
| 4 | O | bond | CH₂CH(CH₃)₂ | CH₃ | 1 | 104–105 |
| 5 | O | O | CH(CH₃)₂ | CH₃ | 1 | 92–93 |
| 6 (Ex. 3) | O | bond | cyclopropyl | CH₃ | 1 | 138–139 |
| 7 | O | bond | 1-CH₃-cyclopropyl | CH₃ | 1 | 81–82 |
| 8 | O | bond | CF₃ | CH₃ | 1 | 82–83 |

INDEX TABLE B

| Cmpd No. | X | Y | Z | R³ | R⁴ | R⁵ | m | mp (°C.) |
|---|---|---|---|---|---|---|---|---|
| 9 | CH | N | COCHF₂ | CH₃ | H | H | 1 | 106–107 |
| 10 | CH | N(O) | CH | CH₃ | H | OCHF₂ | 1 | 120–121 |
| 11 (Ex. 1) | CH | N | CH | CH₃ | H | OCHF₂ | 1 | 154–155 |

INDEX TABLE C

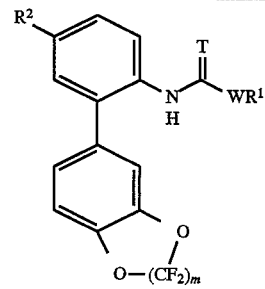

| Cmpd No. | T | W | R¹ | R² | m | mp (°C.) |
|---|---|---|---|---|---|---|
| 12 (Ex. 2) | O | bond | CH₃ | CH₃ | 1 | 105–107 |

TEST A

Seeds of barley (*Hordeum vulgare*), barnyardgrass (*Echinochloa crus-galli*), bedstraw (*Galium aparine*), blackgrass (*Alopecurus myosuroides*), chickweed (*Stellaria media*), cocklebur (*Xanthium pensylvanicum*), corn (*Zea mays*), cotton (*Gossypium hirsutum*), crabgrass (*Digitaria sanguinalis*), downy brome (*Bromus tectorum*), giant foxtail (*Setaria faberii*), lambsquarters (*Chenopodium album*), morningglory (*Ipomoea hederacea*), rape (*Brassica napus*), rice (*Oryza saliva*), sorghum (*Sorghum bicolor*), soybean (*Glycine max*), sugar beet (*Beta vulgaris*), velvetleaf (*Abutilon theophrasti*), wheat (*Triticum aestivum*), wild buckwheat (*Polygonum convolvulus*), wild oat (*Avena fatua*) and purple nutsedge (*Cyperus rotundus*) tubers were planted and treated preemergence with test chemicals formulated in a non-phytotoxic solvent mixture which includes a surfactant.

At the same time, these crop and weed species were also treated with postemergence applications of test chemicals formulated in the same manner. Plants ranged in height from two to eighteen cm (one to four leaf stage) for postemergence treatments. Treated plants and controls were maintained in a greenhouse for twelve to sixteen days, after which all species were compared to controls and visually evaluated. Plant response ratings, summarized in Table A, are based on a scale of 0 to 10 where 0 is no effect and 10 is complete control. A dash (–) response means no test result.

TABLE A

| Rate 1000 g/ha | COMPOUND 1 | 2 | 3 | 4 | Rate 1000 g/ha | COMPOUND 1 | 2 | 3 | 4 |
|---|---|---|---|---|---|---|---|---|---|
| POSTEMERGENCE | | | | | PREEMERGENCE | | | | |
| Barley | 4 | 1 | 8 | 5 | Barley | 3 | 0 | 5 | 3 |
| Barnyardgrass | 9 | 2 | 9 | 9 | Barnyardgrass | 9 | 4 | 9 | 10 |
| Bedstraw | 2 | 6 | 9 | 9 | Bedstraw | 0 | 0 | 8 | 9 |
| Blackgrass | 5 | 2 | 9 | 8 | Blackgrass | 5 | 1 | 10 | 10 |
| Chickweed | 3 | 3 | 8 | 7 | Chickweed | 9 | 0 | 9 | 8 |
| Cocklebur | 2 | 7 | 7 | 6 | Cocklebur | 0 | 0 | 0 | 0 |
| Corn | 8 | 2 | 8 | 6 | Corn | 3 | 0 | 6 | 5 |
| Cotton | 1 | 3 | 8 | 10 | Cotton | 0 | 0 | 1 | 9 |
| Crabgrass | 9 | 2 | 10 | 9 | Crabgrass | 10 | 10 | 10 | 10 |
| Downy brome | 1 | 1 | 9 | 2 | Downy brome | 5 | 1 | 10 | 8 |
| Giant foxtail | 9 | 1 | 9 | 9 | Giant foxtail | 9 | 9 | 10 | 10 |
| Lambsquarter | 8 | 6 | 9 | 9 | Lambsquarter | 9 | 8 | 9 | 10 |
| Morningglory | 5 | 8 | 9 | 10 | Morningglory | 5 | 1 | 8 | 10 |
| Nutsedge | 1 | 0 | 3 | 3 | Nutsedge | 3 | 0 | 3 | 3 |
| Rape | 1 | 3 | 6 | 8 | Rape | 3 | 0 | 6 | 9 |
| Rice | 2 | 2 | 7 | 3 | Rice | 1 | 0 | 3 | 3 |
| Sorghum | 7 | 2 | 7 | 5 | Sorghum | 3 | 1 | 5 | 3 |
| Soybean | 5 | 5 | 7 | 9 | Soybean | 3 | 0 | 6 | 6 |
| Sugar beet | 7 | 7 | 10 | 10 | Sugar beet | 6 | 2 | 10 | 10 |
| Velvetleaf | 9 | 2 | 9 | 8 | Velvetleaf | 6 | 1 | 10 | 10 |
| Wheat | 1 | 2 | 8 | 3 | Wheat | 1 | 0 | 7 | 6 |
| Wild buckwheat | 6 | 3 | 9 | 9 | Wild buckwheat | 2 | 0 | 2 | 7 |
| Wild oat | 5 | 1 | 9 | 8 | Wild oat | 9 | 5 | 10 | 10 |

| Rate 400 g/ha | COMPOUND 9 | 10 | Rate 400 g/ha | COMPOUND 9 | 10 |
|---|---|---|---|---|---|
| POSTEMERGENCE | | | PREEMERGENCE | | |
| Barley | 6 | 3 | Barley | 8 | 1 |
| Barnyardgrass | 5 | 2 | Barnyardgrass | 10 | 3 |
| Bedstraw | 9 | 7 | Bedstraw | 9 | 7 |
| Blackgrass | 4 | 2 | Blackgrass | 9 | 1 |
| Chickweed | 8 | 6 | Chickweed | 9 | 8 |
| Cocklebur | 8 | 4 | Cocklebur | 1 | 0 |
| Corn | 3 | 2 | Corn | 4 | 1 |
| Cotton | 9 | 9 | Cotton | 3 | 3 |
| Crabgrass | 9 | 10 | Crabgrass | 10 | 9 |
| Downy brome | 3 | 1 | Downy brome | 9 | 1 |
| Giant foxtail | 6 | 2 | Giant foxtail | 10 | 6 |
| Lambsquarter | 9 | 9 | Lambsquarter | 9 | 9 |
| Morningglory | 9 | 8 | Morningglory | 5 | 3 |
| Nutsedge | 1 | 0 | Nutsedge | 4 | 0 |
| Rape | 9 | 6 | Rape | 8 | 7 |
| Rice | 3 | 2 | Rice | 3 | 0 |
| Sorghum | 3 | 1 | Sorghum | 3 | 0 |
| Soybean | 6 | 6 | Soybean | 1 | 1 |
| Sugar beet | 9 | 9 | Sugar beet | 10 | 10 |
| Velvetleaf | 6 | 2 | Velvetleaf | 8 | 6 |
| Wheat | 3 | 2 | Wheat | 8 | 0 |
| Wild buckwheat | 7 | 4 | Wild buckwheat | 8 | 3 |
| Wild oat | 5 | 2 | Wild oat | 9 | — |

| Rate 200 g/ha | COMPOUND 1 | 2 | 3 | 4 | Rate 200 g/ha | COMPOUND 1 | 2 | 3 | 4 |
|---|---|---|---|---|---|---|---|---|---|
| POSTEMERGENCE | | | | | PREEMERGENCE | | | | |
| Barley | 1 | 1 | 6 | 2 | Barley | 0 | 0 | 1 | 1 |
| Barnyardgrass | 4 | 1 | 8 | 7 | Barnyardgrass | 3 | 0 | 7 | 6 |
| Bedstraw | 2 | 3 | 7 | 7 | Bedstraw | 0 | 0 | 2 | 4 |
| Blackgrass | 1 | 1 | 6 | 2 | Blackgrass | 2 | 0 | 3 | 2 |
| Chickweed | 3 | 2 | 7 | 5 | Chickweed | 2 | 0 | 6 | 4 |
| Cocklebur | 2 | 3 | 5 | 2 | Cocklebur | 0 | 0 | 0 | 0 |
| Corn | 2 | 1 | 6 | 5 | Corn | 1 | 0 | 4 | 5 |
| Cotton | 1 | 2 | 4 | 9 | Cotton | 0 | 0 | 0 | 0 |
| Crabgrass | 4 | 0 | 10 | 7 | Crabgrass | 8 | 1 | 10 | 10 |
| Downy brome | 1 | 0 | 3 | 1 | Downy brome | 1 | 0 | 2 | 2 |
| Giant foxtail | 4 | 1 | 9 | 6 | Giant foxtail | 7 | 1 | 9 | 9 |
| Lambsquarter | 6 | 2 | 9 | 9 | Lambsquarter | 0 | 0 | 9 | 9 |
| Morningglory | 3 | 7 | 9 | 10 | Morningglory | 1 | 0 | 3 | 3 |
| Nutsedge | 1 | 0 | 1 | 3 | Nutsedge | 0 | 0 | 0 | 3 |
| Rape | 0 | 2 | 2 | 6 | Rape | 0 | 0 | 1 | 9 |
| Rice | 0 | 0 | 4 | 2 | Rice | 0 | 0 | 1 | 1 |
| Sorghum | 0 | 0 | 3 | 1 | Sorghum | 0 | 0 | 2 | 1 |
| Soybean | 3 | 4 | 6 | 8 | Soybean | 0 | 0 | 2 | 3 |
| Sugar beet | 2 | 2 | 9 | 8 | Sugar beet | 3 | 0 | 10 | 10 |
| Velvetleaf | 6 | 1 | 7 | 6 | Velvetleaf | 1 | 0 | 10 | 10 |
| Wheat | 1 | 1 | 2 | 3 | Wheat | 0 | 0 | 2 | 1 |
| Wild buckwheat | 1 | 1 | 6 | 4 | Wild buckwheat | 0 | 0 | 2 | 3 |
| Wild oat | 1 | 0 | 4 | 1 | Wild oat | 2 | 0 | 9 | 7 |

| Rate 100 g/ha | COMPOUND 9 | 10 | Rate 100 g/ha | COMPOUND 9 | 10 |
|---|---|---|---|---|---|
| POSTEMERGENCE | | | PREEMERGENCE | | |
| Barley | 3 | 3 | Barley | 0 | 0 |
| Barnyardgrass | 3 | 1 | Barnyardgrass | 1 | 1 |
| Bedstraw | 7 | 3 | Bedstraw | 1 | 1 |
| Blackgrass | 2 | 2 | Blackgrass | 1 | 0 |
| Chickweed | 4 | 3 | Chickweed | 3 | 5 |
| Cocklebur | 7 | 3 | Cocklebur | 0 | 0 |
| Corn | 2 | 1 | Corn | 1 | 0 |
| Cotton | 9 | 9 | Cotton | 0 | 0 |
| Crabgrass | 7 | 9 | Crabgrass | 9 | 2 |
| Downy brome | 1 | 1 | Downy brome | 2 | 0 |
| Giant foxtail | 2 | 1 | Giant foxtail | 8 | 1 |
| Lambsquarter | 8 | 9 | Lambsquarter | 6 | 8 |
| Morningglory | 9 | 1 | Morningglory | 0 | 2 |
| Nutsedge | 0 | 0 | Nutsedge | 0 | 0 |
| Rape | 7 | 8 | Rape | 1 | 3 |
| Rice | 3 | 1 | Rice | 0 | 0 |
| Sorghum | 2 | 1 | Sorghum | 0 | 0 |
| Soybean | 4 | 4 | Soybean | 0 | 0 |
| Sugar beet | 9 | 9 | Sugar beet | 2 | 6 |
| Velvetleaf | 3 | 1 | Velvetleaf | 1 | 1 |
| Wheat | 2 | 2 | Wheat | 1 | 0 |
| Wild buckwheat | 5 | 2 | Wild buckwheat | 1 | 0 |
| Wild oat | 2 | 2 | Wild oat | 6 | 1 |

What is claimed is:

1. A compound selected from Formula I, an N-oxide and an agriculturally-suitable salt thereof,

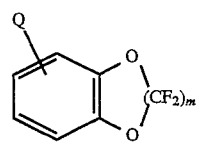

I wherein:

Q is

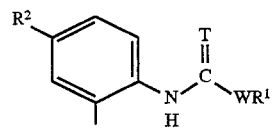

Q-1

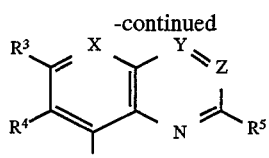

Q-2

T is O or S;
W is a single bond, O, S or NR$^6$;
X is N or CH;
Y is N or CH;
Z is N or CR$^7$ provided that when Z is CR$^7$, then Y is N;
R$^1$ is C$_1$-C$_5$ alkyl optionally substituted with C$_1$-C$_2$ alkoxy, OH, 1-3 halogens, or C$_1$-C$_2$ alkylthio; CH$_2$(C$_3$-C$_4$ cycloalkyl); C$_3$-C$_4$ cycloalkyl optionally substituted with 1-3 methyl groups; C$_2$-C$_4$ alkenyl; C$_2$-C$_4$ haloalkenyl; or phenyl optionally substituted with halogen, C$_1$-C$_4$ alkyl, C$_1$-C$_4$ haloalkyl, C$_1$-C$_4$ alkoxy, C$_1$-C$_4$ haloalkoxy, nitro or cyano;
R$^2$ is H, chlorine, bromine, C$_1$-C$_2$ alkyl, C$_1$-C$_2$ alkoxy, C$_1$-C$_2$ alkylthio, C$_2$-C$_3$ alkoxyalkyl, C$_2$-C$_3$ alkylthioalkyl, cyano, nitro, NH(C$_1$-C$_2$ alkyl) or N(C$_1$-C$_2$ alkyl)$_2$;
R$^3$ is C$_1$-C$_4$ alkyl, C$_2$-C$_4$ alkoxyalkyl, C$_2$-C$_4$ alkenyl, C$_2$-C$_4$ alkynyl, C$_1$-C$_4$ alkoxy, C$_1$-C$_4$ alkylthio, C$_1$-C$_3$ alkylamino or N(C$_1$-C$_3$ alkyl)(C$_1$-C$_3$ alkyl);
R$^4$ is H or F;
R$^5$ is H, CN, C$_1$-C$_3$ alkyl, C$_1$-C$_4$ haloalkyl, C$_3$-C$_4$ halocycloalkyl, C$_2$-C$_4$ haloalkenyl, C$_3$-C$_4$ haloalkynyl, OR$^8$, S(O)$_n$R$^9$ or halogen;
R$^6$ is H, CH$_3$ or OCH$_3$;
R$^7$ is H, CN, C$_1$-C$_3$ alkyl, C$_1$-C$_4$ haloalkyl, C$_3$-C$_4$ halocycloalkyl, C$_2$-C$_4$ haloalkenyl, C$_3$-C$_4$ haloalkynyl, OR$^{10}$, S(O)$_p$R$^{11}$ or halogen;
R$^8$ and R$^{10}$ are each independently C$_1$-C$_4$ alkyl, C3-C$_4$ alkenyl, C$_3$-C$_4$ alkynyl, C$_1$-C$_4$ haloalkyl, C$_2$-C$_4$ haloalkenyl or C$_3$-C$_4$ haloalkynyl;
R$^9$ and R$^{11}$ are each independently C$_1$-C$_2$ alkyl or C$_1$-C$_2$ haloalkyl;
m is 1 or 2; and
n and p are each independently 0, 1 or 2;
provided that when Z is CR$^7$, then exactly one of R$^5$ and R$^7$ is H.

2. A compound of claim 1 wherein:

R$^1$ is C$_1$-C$_4$ alkyl optionally substituted with methoxy or 1-3 halogens; C$_2$-C$_4$ alkenyl; or C$_2$-C$_4$ haloalkenyl;
R$^2$ is chlorine, bromine, C$_1$-C$_2$ alkyl, C$_1$-C$_2$ alkoxy, cyano, nitro, NH(C$_1$-C$_2$ alkyl) or N(C$_1$-C$_2$ alkyl)$_2$; and
R$^3$ is C$_1$-C$_3$ alkyl, C$_2$-C$_3$ alkoxyalkyl, C$_2$-C$_3$ alkenyl, C$_2$-C$_3$ alkynyl, C$_1$-C$_2$ alkoxy, C$_1$-C$_2$ alkylthio, C$_1$-C$_2$ alkylamino or N(C$_1$-C$_2$ alkyl)(C$_1$-C$_2$ alkyl);
R$^7$ is H, C$_1$-C$_2$ haloalkyl, OR$^{10}$, or S(O)$_p$R$^{11}$;
R$^{10}$ is C$_1$-C$_2$ haloalkyl;
R$^{11}$ is C$_1$ haloalkyl; and
p is 0.

3. A compound of claim 2 wherein:

T is O;
W is a single bond;
m is 1; and
n is 0.

4. A compound of claim 3 wherein:

R$^5$ is H, C$_1$-C$_2$ haloalkyl, OR$^8$, or SR$^9$;
R$^7$ is H, CF$_3$, or OR$^{10}$;
R$^8$ is C$_1$-C$_2$ haloalkyl;
R$^9$ is C$_1$ haloalkyl; and
R$^{10}$ is CF$_2$H.

5. The compound of claim 4 selected from the group:

N-[2-(2,2-difluoro-1,3-benzodioxol-4-yl)-4-methylphenyl]-2-methylpropanamide; and 8-(2,2-difluoro-1,3-benzodioxol-4-yl)-2-(difluoromethoxy)-6-methylquinoxaline.

6. A herbicidal composition comprising a herbicidally effective amount of a compound of claim 1 and at least one of a surfactant, a solid diluent or a liquid diluent.

7. A method for controlling the growth of undesired vegetation comprising contacting the vegetation or its environment with a herbicidally effective amount of a composition of claim 6.

* * * * *